(12) United States Patent
Kobayashi et al.

(10) Patent No.: US 12,208,935 B2
(45) Date of Patent: Jan. 28, 2025

(54) WRAP REPLACING APPARATUS

(71) Applicant: Canon Medical Systems Corporation, Otawara (JP)

(72) Inventors: Yoshimasa Kobayashi, Nasushiobara (JP); Yasuhiro Sugawara, Nasushiobara (JP); Seiichi Nishizuka, Nasushiobara (JP); Takehiro Fukuzaki, Utsunomiya (JP); Daisuke Sato, Utsunomiya (JP); Tatsuaki Kodaka, Nasushiobara (JP); Akitoshi Sato, Otawara (JP); Tomio Maehama, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 127 days.

(21) Appl. No.: 17/552,023

(22) Filed: Dec. 15, 2021

(65) Prior Publication Data

US 2022/0185524 A1    Jun. 16, 2022

(30) Foreign Application Priority Data

Dec. 15, 2020   (JP) .................................. 2020-207321
Dec. 14, 2021   (JP) .................................. 2021-202505

(51) Int. Cl.
*B65B 67/04*     (2006.01)
*A61B 50/30*     (2016.01)
(Continued)

(52) U.S. Cl.
CPC .............. *B65B 67/04* (2013.01); *A61B 50/30* (2016.02); *B65B 5/045* (2013.01); *B65B 53/02* (2013.01);
(Continued)

(58) Field of Classification Search
CPC ......... B65B 67/04; B65B 5/045; B65B 53/02; B65B 69/00; A61B 50/30; A61B 6/4405; A61B 8/4427
(Continued)

(56) References Cited

U.S. PATENT DOCUMENTS 6,065,272 A * 5/2000 Lecomte ............. B29C 66/8221
                                                    53/567
7,389,630 B2 * 6/2008 Nakano .................. B29C 66/43
                                                    53/553
(Continued)

FOREIGN PATENT DOCUMENTS

JP      2008-50047 A       3/2008
JP      2012-123297 A      6/2012
(Continued)

OTHER PUBLICATIONS

Combine Chinese Office Action and Search Report issued Apr. 11, 2024 in Chinese Patent Application No. 202111534082.4 (with English Translation of Category of Cited Documents), 7 pages.

*Primary Examiner* — Robert F Long
*Assistant Examiner* — Xavier A Madison
(74) *Attorney, Agent, or Firm* — Oblon, McClelland, Maier & Neustadt, L.L.P.

(57) ABSTRACT

A wrap replacing apparatus according to the embodiments includes: an insertion port into which a medical device wrapped in a first bag is inserted; a peeler configured to peel off the first bag from the medical device inserted into the insertion port; a wrapper configured to wrap in a second bag the medical device from which the first bag is peeled off; and a take-out port from which the medical device wrapped in the second bag is taken out.

14 Claims, 19 Drawing Sheets

(51) Int. Cl.
   *B65B 5/04* (2006.01)
   *B65B 53/02* (2006.01)
   *B65B 69/00* (2006.01)
   *A61B 6/00* (2006.01)
   *A61B 8/00* (2006.01)

(52) U.S. Cl.
   CPC ............ *B65B 69/00* (2013.01); *A61B 6/4405* (2013.01); *A61B 8/4427* (2013.01)

(58) Field of Classification Search
   USPC .......................................................... 53/557
   See application file for complete search history.

(56) References Cited

U.S. PATENT DOCUMENTS

| | | | | |
|---|---|---|---|---|
| 7,827,770 | B2* | 11/2010 | Rocholl | B65B 69/0008 414/412 |
| 2008/0101901 | A1 | 5/2008 | Rocholl et al. | |
| 2013/0318914 | A1* | 12/2013 | Takata | B65B 5/045 53/203 |

FOREIGN PATENT DOCUMENTS

| | | |
|---|---|---|
| JP | 2012-215699 A | 11/2012 |
| JP | 2013-248124 A | 12/2013 |

* cited by examiner

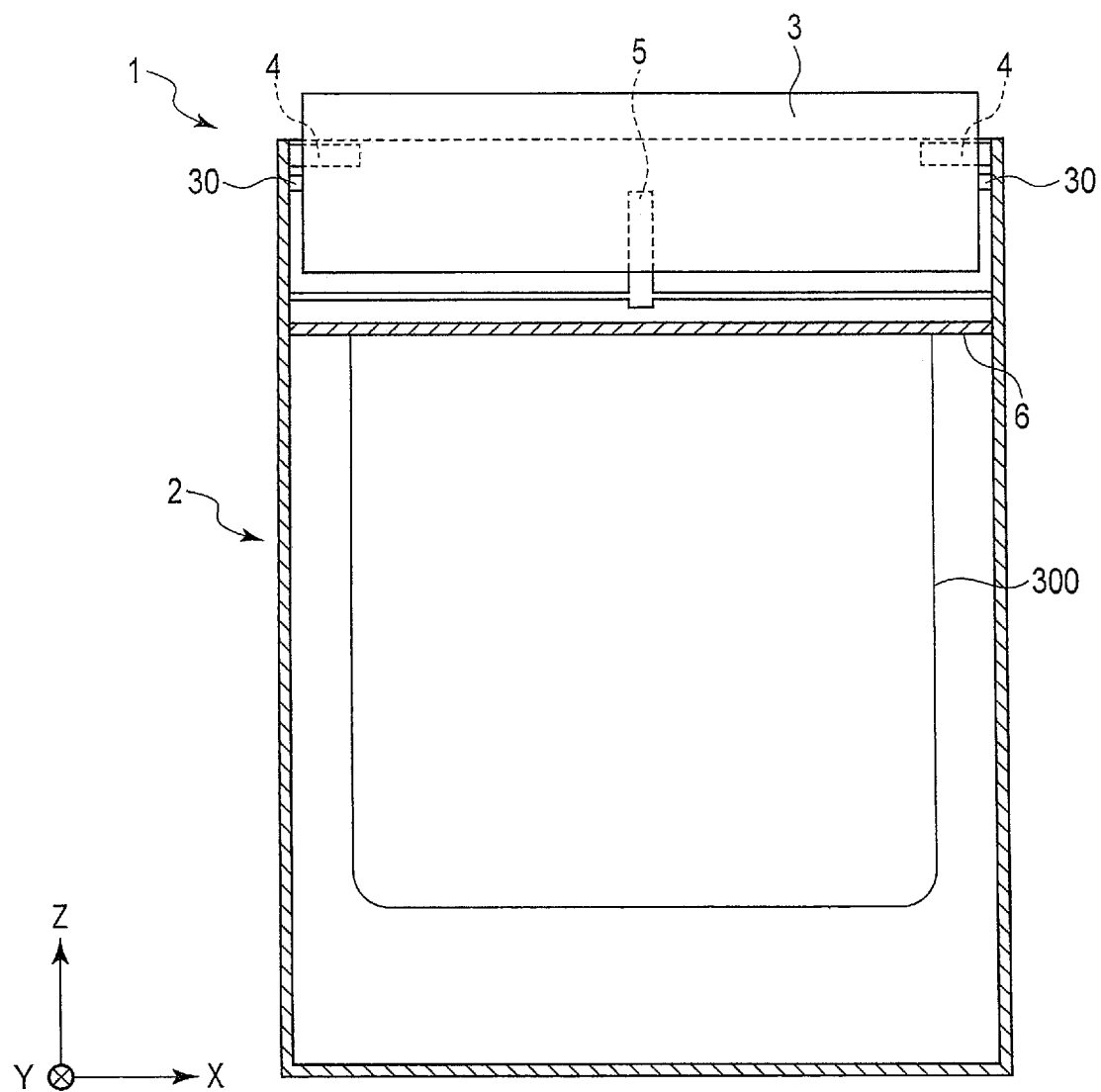
F I G. 5

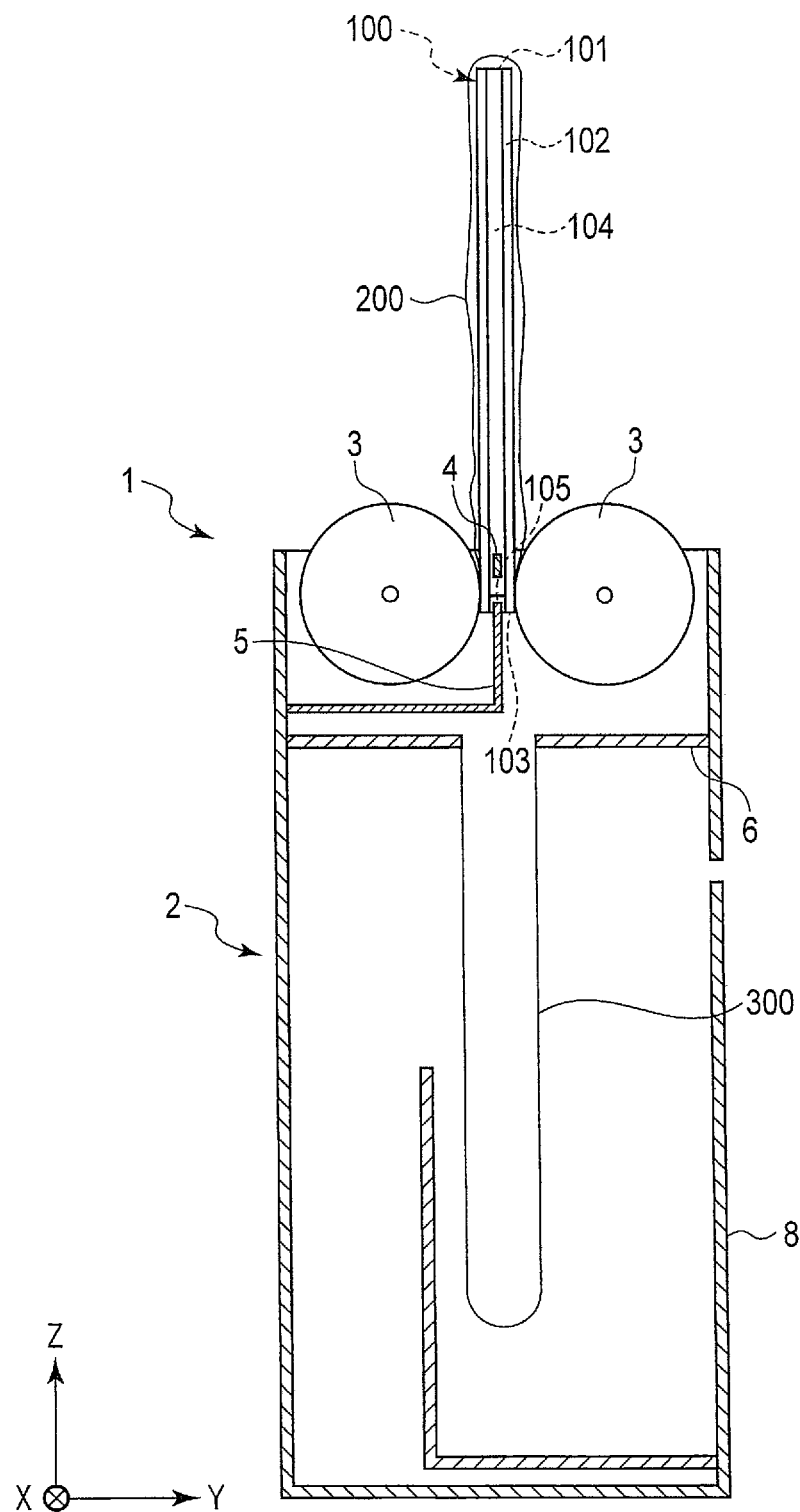
F I G. 6

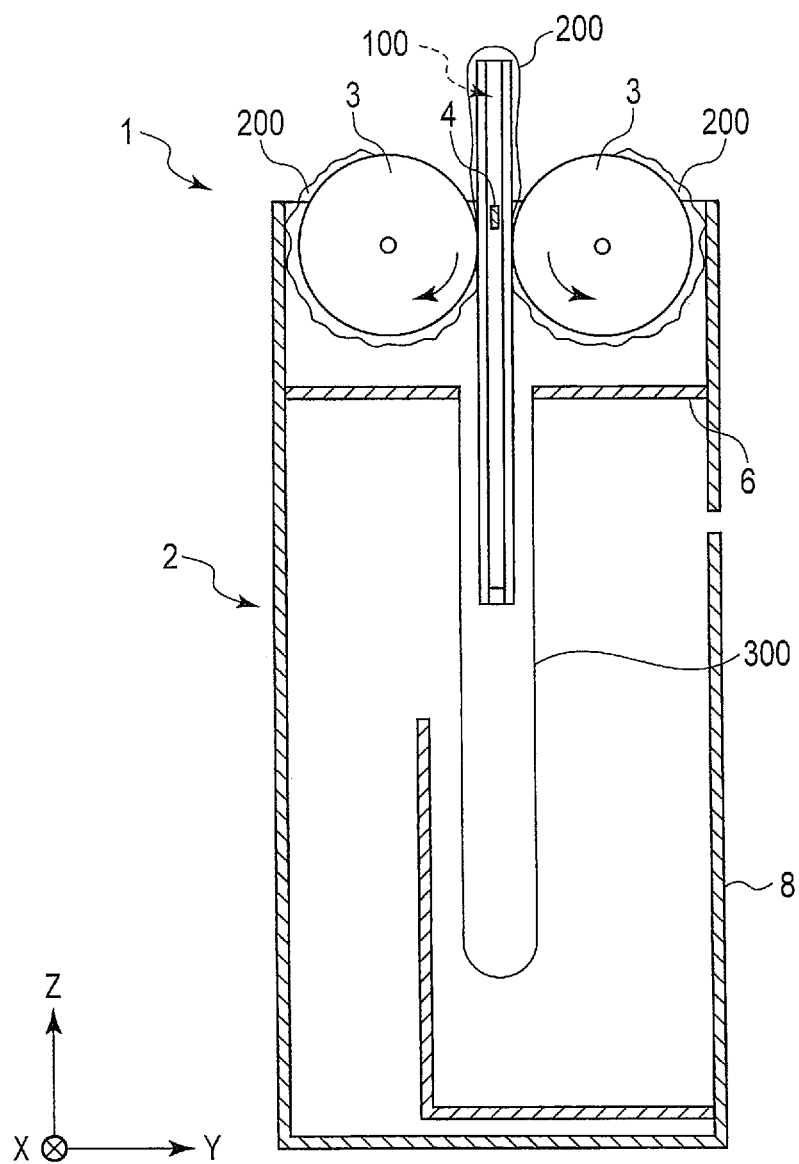
F I G. 7

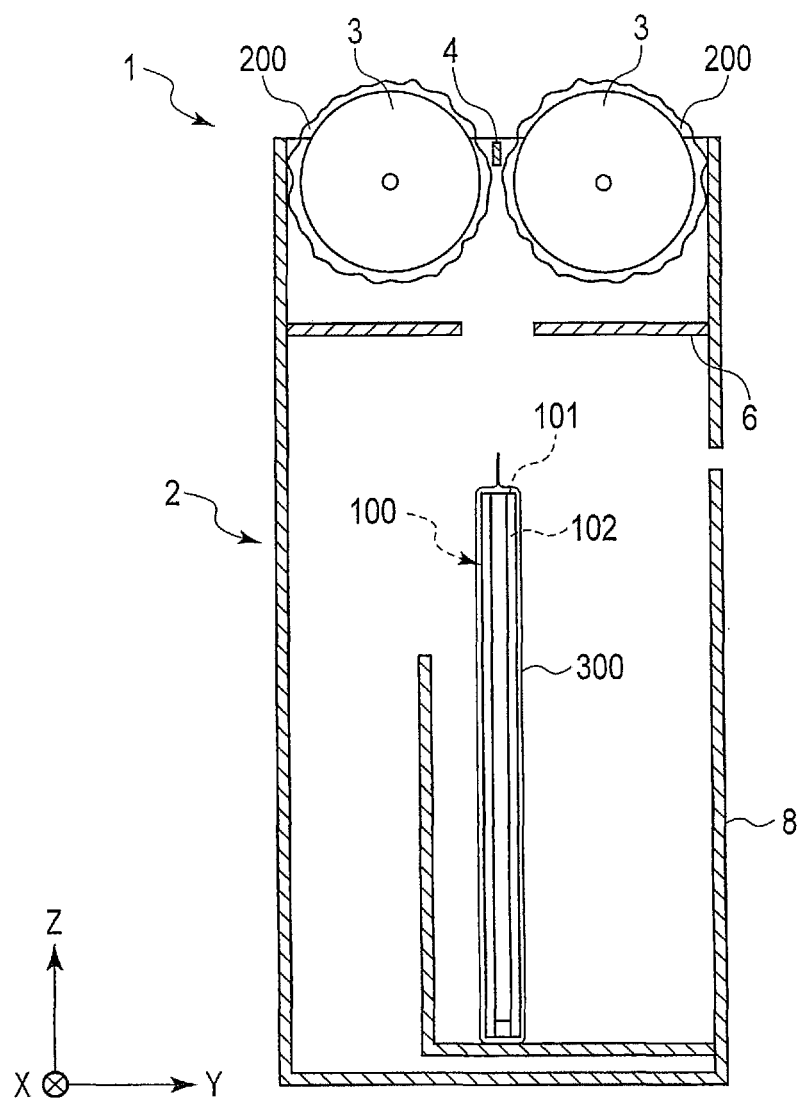
F I G. 8

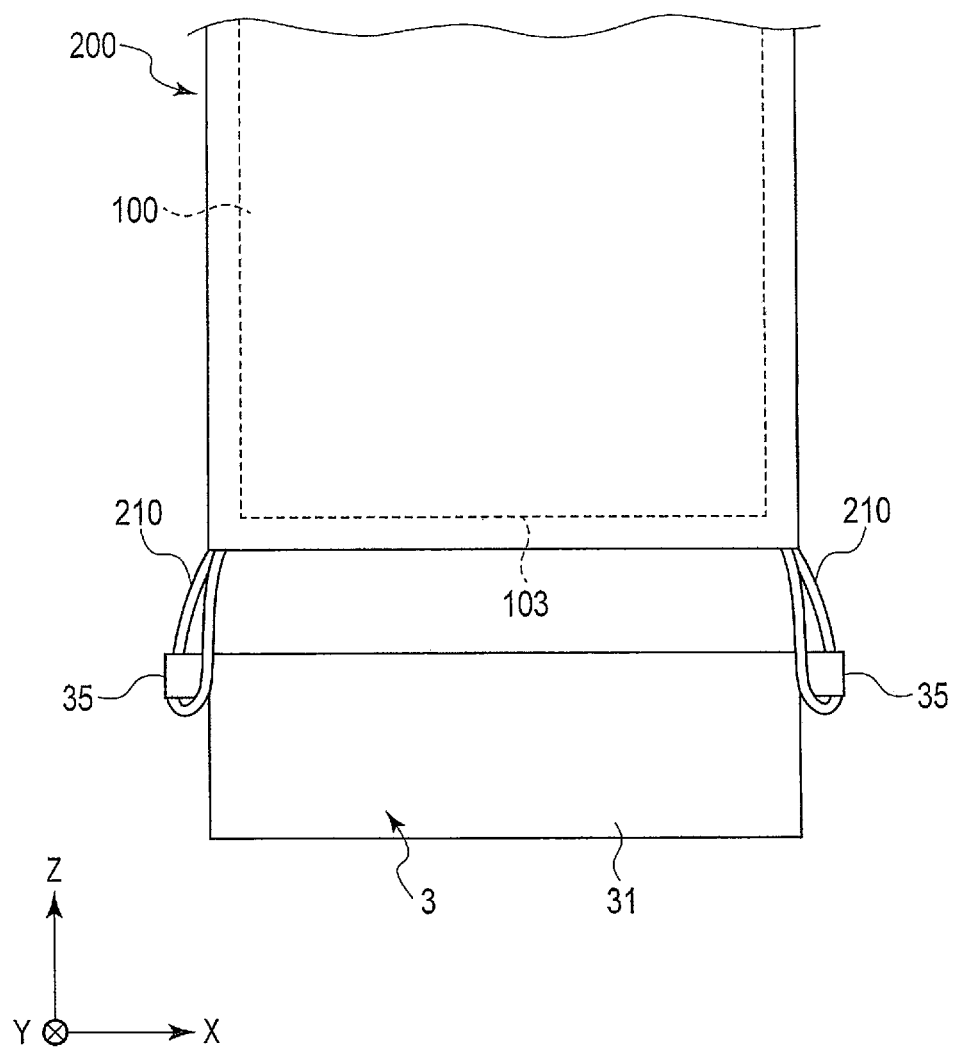
F I G. 12

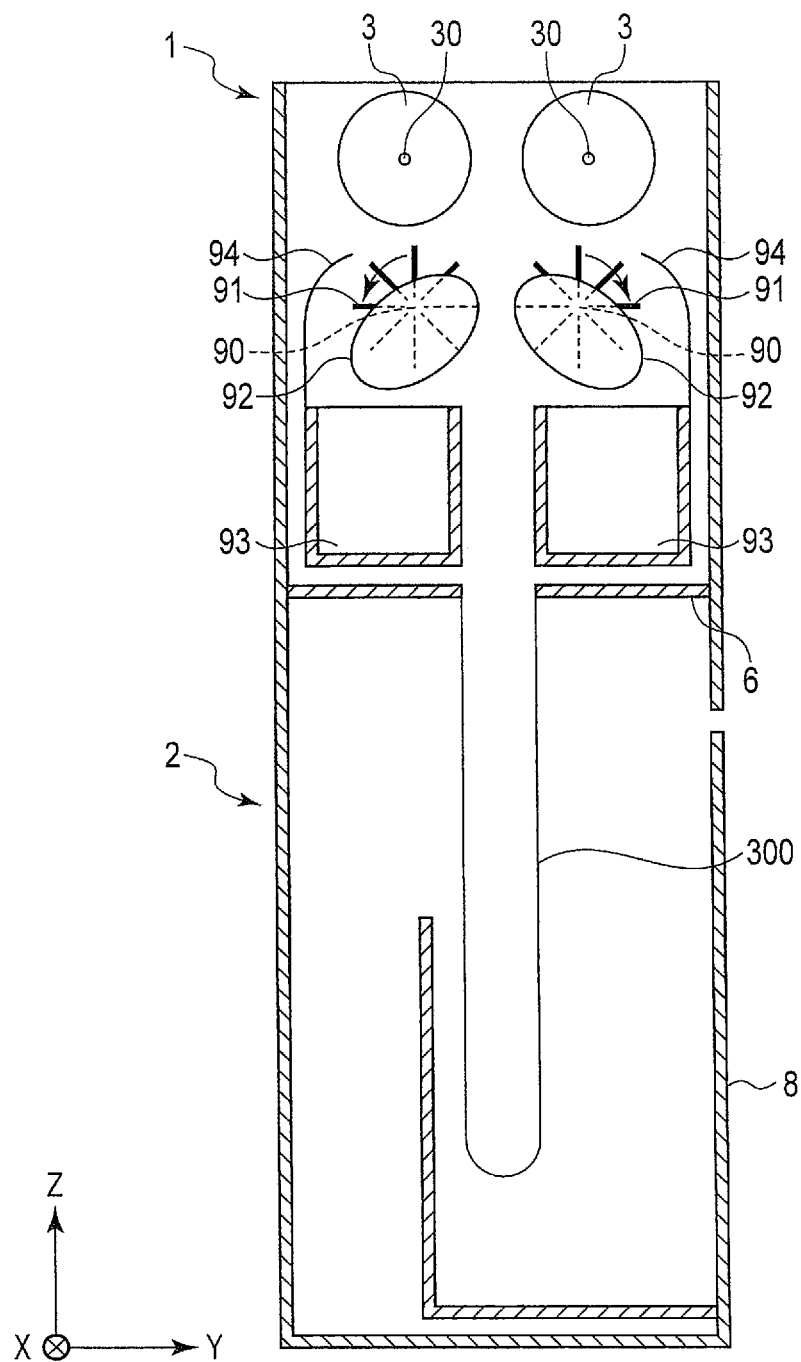
F I G. 21

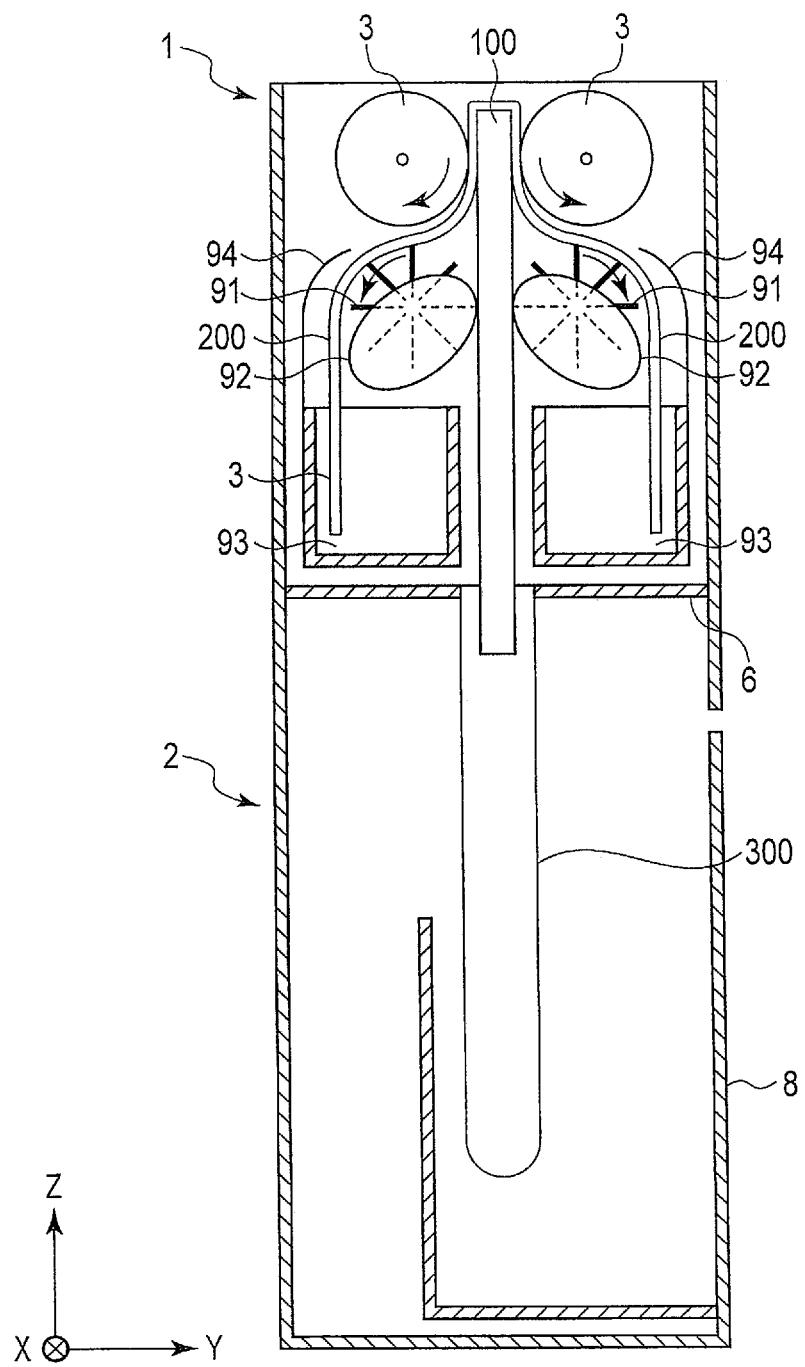
F I G. 23

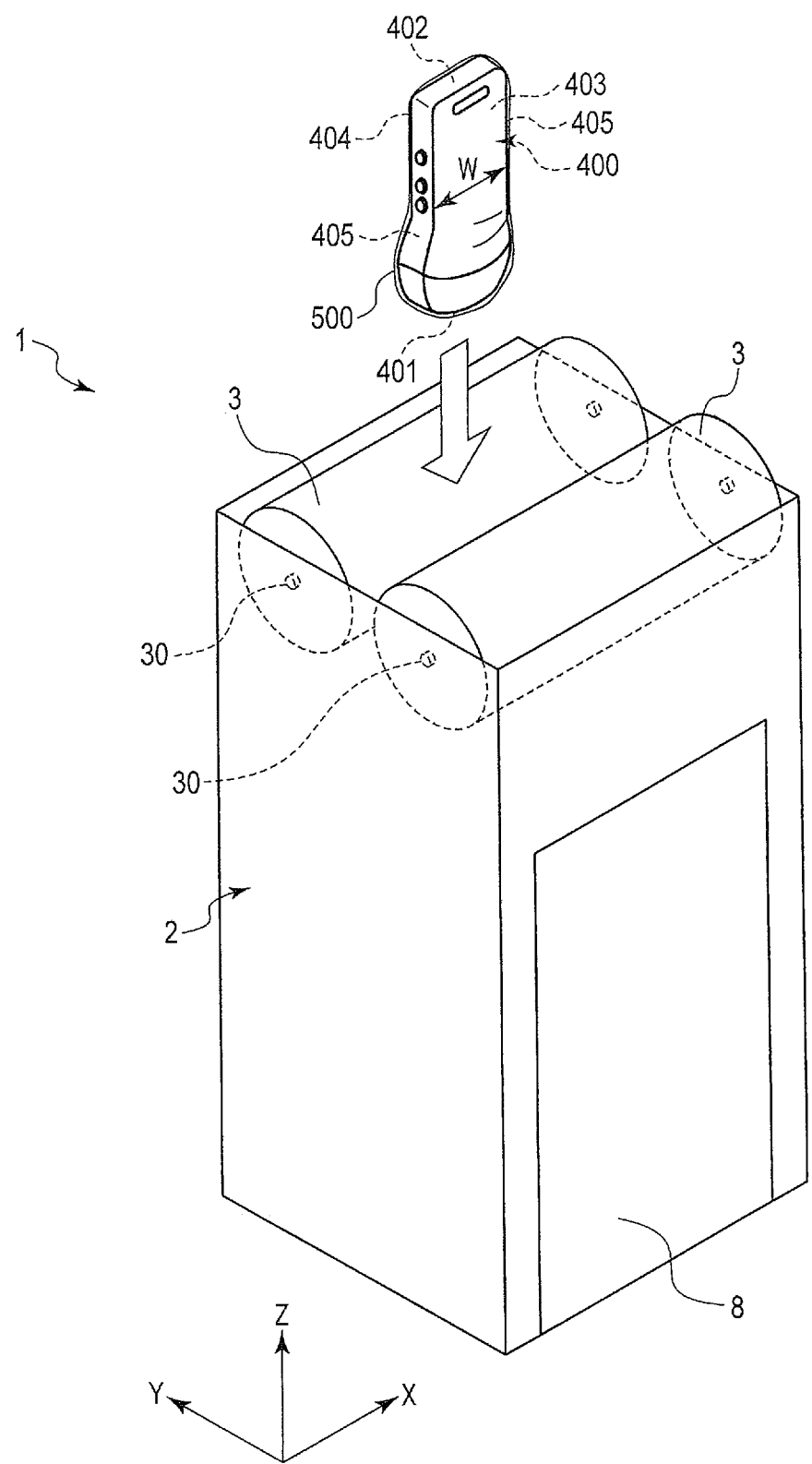
F I G. 24

WRAP REPLACING APPARATUS

CROSS-REFERENCE TO RELATED APPLICATIONS

This application is based upon and claims the benefit of priority from Japanese Patent Applications No. 2020-207321, filed Dec. 15, 2020; and No. 2021-202505, filed Dec. 14, 2021; the entire contents of all of which are incorporated herein by reference.

FIELD

Embodiments described herein relate generally to a wrap replacing apparatus.

BACKGROUND

A portable X-ray apparatus is used when X-ray imaging is performed in follow-up observation of Coronavirus Disease 2019 (COVID-19) patients. The portable X-ray apparatus is also used as a guide for Extra Corporeal Membrane Oxygenation (VV-ECMO) with respect to COVID-19 patients. In the case of performing X-ray imaging using a portable X-ray apparatus, in order to prevent infection, X-ray imaging is performed in a state in which a Flat Panel Detector (FPD) used as an X-ray detector is wrapped in a plastic bag and then another plastic bag. Every time imaging of one patient is completed, only the outer plastic bag is replaced with a new sterilized plastic bag. When replacing the outer plastic bag, in order to prevent infection, replacement needs to be performed without touching the inner plastic bag. For this reason, first, one operator removes about half of the outer plastic bag. Then, with a new plastic bag ready, another operator receives the FPD wrapped in the inner plastic bag. In this manner, rewrapping with only the outer plastic bag is performed without touching the inner plastic bag. This case requires the above operation, which requires two operators. The above operation is demanding because it requires caution and attention.

BRIEF DESCRIPTION OF THE DRAWINGS

FIG. 5 is a diagram showing the internal configuration of the wrap replacing apparatus according to the first embodiment.

FIG. 6 is a diagram showing a state in which the X-ray detector is inserted between rollers of the wrap replacing apparatus according to the first embodiment.

FIG. 7 is a diagram showing a state in which a first bag is peeled off from the X-ray detector inserted into the wrap replacing apparatus according to the first embodiment.

FIG. 8 is a diagram showing a state in which an opening of a second bag fixed to the wrap replacing apparatus according to the first embodiment is sealed.

FIG. 12 is a diagram showing a state immediately before the X-ray detector wrapped in the first bag is inserted between rollers in the wrap replacing apparatus according to the second embodiment.

FIG. 21 is a diagram showing an internal configuration of a wrap replacing apparatus according to a third embodiment.

FIG. 23 is a diagram showing a state in which an X-ray detector wrapped in a first bag is conveyed in the wrap replacing apparatus according to the third embodiment.

FIG. 24 is a diagram showing a configuration of a wrap replacing apparatus according to a fourth embodiment.

DETAILED DESCRIPTION

A wrap replacing apparatus according to the embodiments includes: an insertion port into which a medical device wrapped in a first bag is inserted; a peeler configured to peel off the first bag from the medical device inserted into the insertion port; a wrapper configured to wrap in a second bag the medical device from which the first bag is peeled off; and a take-out port from which the medical device wrapped in the second bag is taken out.

Hereinafter, the embodiments of a wrap replacing apparatus will be described in detail with reference to the drawings. The wrap replacing apparatus can peel off a used bag from the medical device wrapped in the used bag and wrap in a new bag the medical device from which the used bag has been peeled off. Examples of the medical device include a portable device such as an X-ray detector, an ultrasound probe, etc. In the following description, structural elements having approximately the same function and configuration will be assigned the same reference symbol, and a repeat description will be given only where necessary.

First Embodiment

Figure 1:
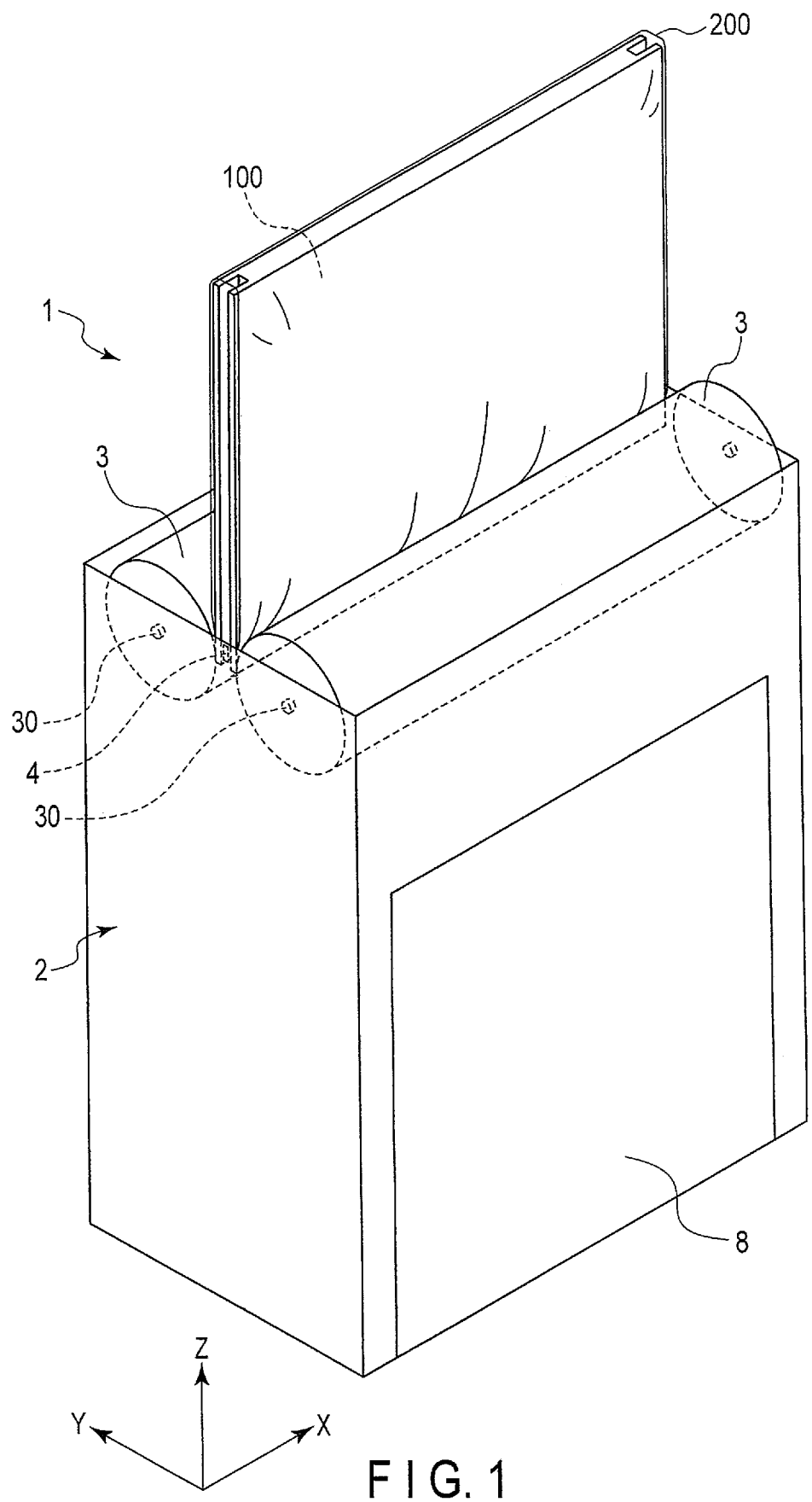
FIG. 1 is a diagram showing a configuration of a wrap replacing apparatus according to a first embodiment.
Figure 2:
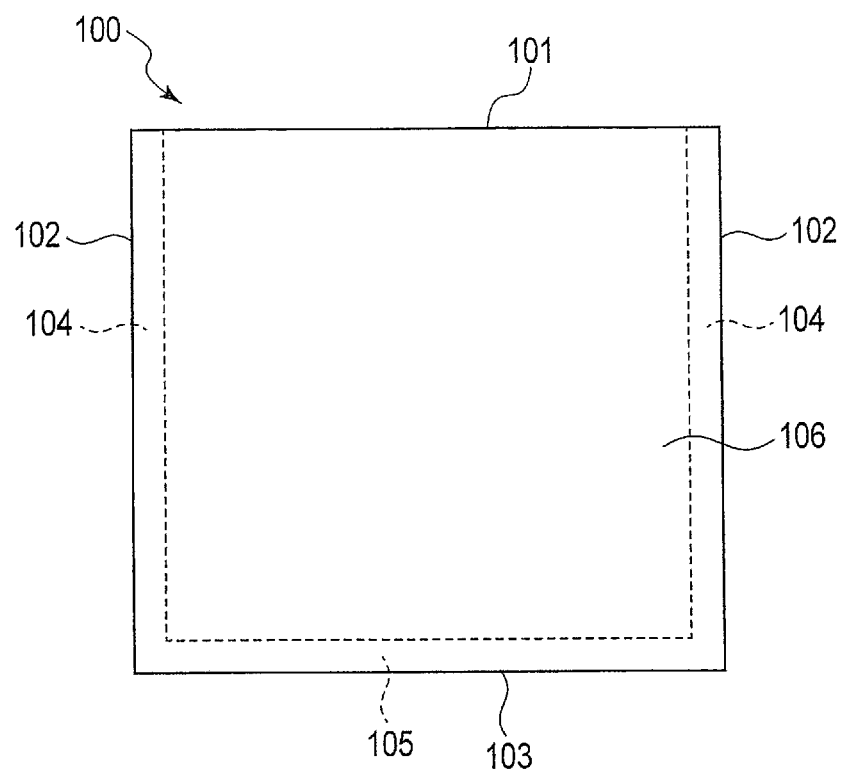
FIG. 2 is a diagram of an X-ray detector that uses the wrap replacing apparatus according to the first embodiment as viewed from a front surface side.
Figure 3:
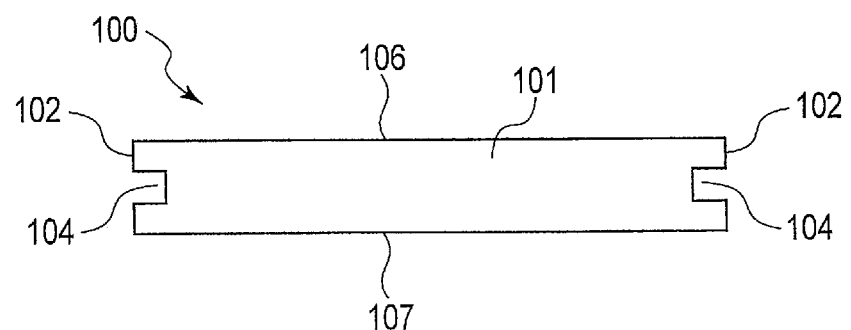
FIG. 3 is a diagram of the X-ray detector that uses the wrap replacing apparatus according to the first embodiment as viewed from a top surface side.
Figure 4:
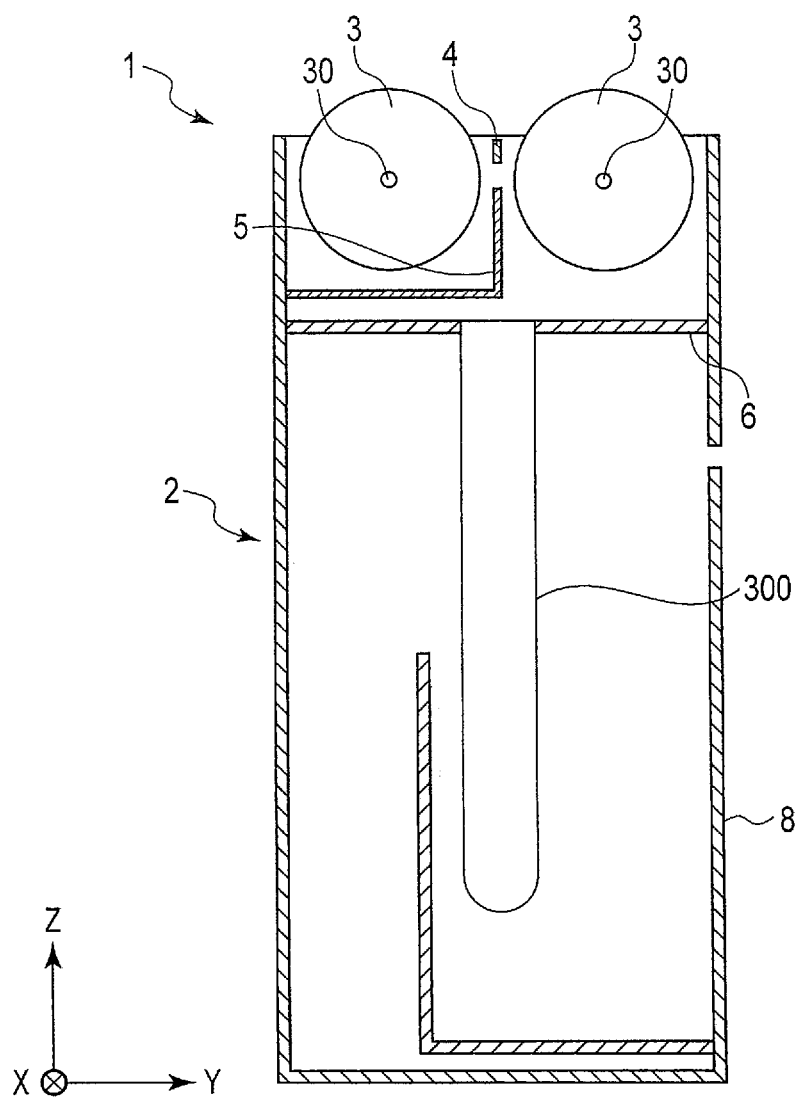
FIG. 4 is a diagram showing an internal configuration of the wrap replacing apparatus according to the first embodiment.

FIG. 1 is a diagram showing a configuration of a wrap replacing apparatus 1 according to the present embodiment. The wrap replacing apparatus 1 according to the present embodiment replaces a wrap that wraps a Flat Panel Detector (hereinafter, referred to as FPD) 100 used as an X-ray detector. FIG. 2 and FIG. 3 are diagrams each showing a configuration of the FPD 100. FIG. 4 and FIG. 5 are diagrams each showing the internal configuration of the wrap replacing apparatus 1. The wrap replacing apparatus 1 is an apparatus that peels off a first bag 200 from an FPD 100 wrapped in the first bag 200 and automatically wraps the FPD 100 in a second bag 300. The wrap replacing apparatus 1 may be referred to as an automatic wrapping apparatus, too. The FPD 100 is a planar X-ray detector used in X-ray imaging using a portable X-ray apparatus. The FPD 100 converts X-rays emitted to a subject and transmitted therethrough into electric charges and accumulates them. The size of the FPD 100 falls within the range of 8 to 16 inches, for example. The FPD 100 includes microsensor elements arranged two-dimensionally in the column direction and the line direction. The sensor elements each include a photoelectric film, a charge accumulation capacitor, and a thin film transistor (TFT). The photoelectric film senses X-rays and generates electric charges according to the amount of incident X-rays. The charge accumulation capacitor accumulates the electric charges generated in the photoelectric film. The TFT outputs, at predetermined timings, the electric charges accumulated in the charge accumulation capacitor.

The first bag 200 and the second bag 300 are sterilized covers configured to wrap the FPD 100 in order to prevent infection during X-ray examinations on patients with infectious diseases such as COVID-19. The first bag 200 is, for example, a used plastic bag attached to the FPD 100 used for X-ray imaging performed on an infectious disease patient. The second bag 300 is a new sterilized plastic bag that has not been used so far.

As shown in FIG. 2 and FIG. 3, the FPD 100 is formed into a plate shape. The FPD 100 includes an upper surface 101, two side surfaces 102, a bottom surface 103, a front surface 106, and a back surface 107. The upper surface 101 is a surface facing the side opposite to the bottom surface 103, and is a surface that is inserted lastly into the wrap replacing apparatus 1. The bottom surface 103 is the surface that is inserted firstly into the wrap replacing apparatus 1. One side surface 102 is a surface facing the side opposite to the other side surface 102.

The front surface 106 includes a detection surface on which the detection elements described in the above are disposed, and is a surface facing the side opposite to the back surface 107. The front surface 106 and the back surface 107 form the widest surface on the surface of the FPD 100.

Herein, the direction in which the upper surface 101 or the bottom surface 103 faces is defined as the height direction of the FPD 100, the direction in which the side surfaces 102 faces is defined as the width direction of the FPD 100, and the direction in which the front surface 106 and the back surface 107 face is defined as the thickness direction of the FPD 100. FIG. 2 is a diagram of the FPD 100 viewed from the front surface 106 side in the thickness direction. FIG. 3 is a diagram of the FPD 100 viewed from the upper surface 101 side.

A groove 104 is provided in each of the side surfaces 102. The groove 104 is a recess recessed inward from the corresponding side surface 102 in the width direction. The groove 104 is provided in the central portion of the corresponding side surface 102 in the thickness direction, and extends along the height direction. The groove 104 is provided across the whole corresponding side surface 102 in the height direction.

A groove 105 is provided in the bottom surface 103. The groove 105 is a recess recessed from the bottom surface 103 toward the upper surface 101 in the height direction. The groove 105 is provided in the central portion of the bottom surface 103 in the thickness direction, and extends along the width direction. The groove 105 is provided across the whole bottom surface 103 in the width direction.

With a plastic bag being attached to the FPD 100, the plastic bag comes into close contact with the surface of the FPD 100 from the outside. However, in the portions provided with the grooves 104, the plastic bag does not come into contact with the surfaces of the side surfaces 102, and gaps are formed between the plastic bag and the bottom surfaces of the grooves 104. Similarly, in the portion provided with the groove 105, the plastic bag does not come into contact with the surface of the bottom surface 103, and a gap is formed between the plastic bag and the bottom surface of the groove 105.

Next, the internal configuration of the wrap replacing apparatus 1 will be described in detail. As shown in FIG. 4 and FIG. 5, the wrap replacing apparatus 1 further includes a housing 2, a pair of rollers 3, a side surface incision mechanism 4, a bottom surface incision mechanism 5, a wrapping mechanism 6, and a take-out port 8.

The rollers 3 function as an insertion port into which the FPD 100 is inserted. The FPD 100 wrapped in the first bag 200 is inserted between the pair of rollers 3. The pair of rollers 3 sandwich and hold the FPD 100 wrapped in the first bag 200. Each of the rollers 3 in a pair of rollers 3 has a shaft member 30 which is a central axis, and rotates about the central axis with respect to the housing 2. The pair of rollers 3 rotates while holding the FPD 100 wrapped in the first bag 200, thereby conveying the FPD 100 downward. The pair of rollers 3 function as a conveyer for conveying the FPD 100 wrapped in the first bag 200.

Herein, the direction extending along the central axis of each of the rollers 3 is defined as the X axis. The direction perpendicular to the X axis and horizontal to the X axis is defined as the Y axis. The direction perpendicular to each of the X axis and the Y axis is defined as the Z axis. The Z axis coincides with the vertical direction. FIG. 4 is a diagram showing the internal configuration of the wrap replacing apparatus 1 in a cross section perpendicular to the X axis. FIG. 5 is a diagram showing the internal configuration of the wrap replacing apparatus 1 in a cross section perpendicular to the Y axis.

The side surface incision mechanism 4 and the bottom surface incision mechanism 5 each incise the first bag 200 in which the FPD 100 conveyed by the rollers 3 is wrapped, along the grooves 104 and 105 provided in the FPD 100. The side surface incision mechanism 4 and the bottom surface incision mechanism 5 correspond to an inciser.

The side surface incision mechanism 4 is fixed to the upper side of the shafts 30 of the rollers 3. While the side surface incision mechanism 4 is disposed inside each groove 104, the FPD 100 is conveyed downward by the rollers 3. In this manner, the side surface incision mechanism 4 incises portions that are included in the first bag 200 and are attached to the side surfaces 102 of the FPD 100.

While the FPD 100 is sandwiched and held between the rollers 3, the bottom surface incision mechanism 5 moves inside the groove 105 in the width direction of the FPD 100. In this manner, the bottom surface incision mechanism 5 incises a portion that is included in the first bag 200 and is attached to the bottom surface 103 of the FPD 100.

Furthermore, the rollers 3 convey the FPD 100 downward while peeling the first bag 200 from the FPD 100 incised by the side surface incision mechanism 4 and the bottom surface incision mechanism 5, thereby winding up the peeled off first bag 200. The pair of rollers 3 correspond to a peeler.

The wrapping mechanism 6 fixes the second bag 300. The FPD 100 from which the first bag 200 has been peeled off by the rollers 3 is inserted into the second bag 300 fixed by the wrapping mechanism 6. The wrapping mechanism 6 correspond to a wrapper.

The take-out port 8 is provided at a position different from the insertion port into which the FPD 100 is inserted. That is, the take-out port 8 is provided at a position different from the portion provided with the rollers 3 in the housing 2. At the take-out port 8, the FPD 100 wrapped in the second bag 300 is taken out from the inside of the housing 2. Herein, in the Y axis direction, the side to which the take-out port 8 is attached is defined as the front side. In the Y axis direction, the side on which the take-out port 8 is not attached is defined as the back side.

Furthermore, the wrap replacing apparatus 1 includes a control device. The control device includes a processing circuit and a memory.

The memory is a storage device such as a hard disk drive (HDD), a solid state drive (SSD), an integrated circuit storage unit, etc., configured to store various kinds of information. The memory may be not only an HDD or SDD, but also a portable storage medium, such as a compact disc (CD), a digital versatile disc (DVD), a flash memory, etc. The memory may also be, for example, a drive unit that reads and writes various types of information from and to, e.g., a semiconductor memory device such as a flash memory, a random access memory (RAM), etc.

The processing circuit takes total control over operations of the wrap replacing apparatus 1. The processing circuit is a processor that controls operations and driving of each of the structural elements of the wrap replacing apparatus 1.

The term "processor" used in the above description means, for example, a circuit such as a central processing unit (CPU), a graphics processing unit (GPU), an ASIC, or a programmable logic device (for example, a simple programmable logic device (SPLD), a complex programmable logic device (CPLD), or a field programmable gate array (FPGA)). The processor reads programs stored in the memory and executes them to implement corresponding functions. The programs may be incorporated directly in circuits of the processor, instead of being stored in the memory. In this case, the processor reads and executes a program integrated into the circuit to implement the corresponding function. Each processor of the present embodiment is not limited to a configuration as a single circuit; a plurality of independent circuits may be combined into one processor to implement the function of the processor. The above description of the "processor" is applicable to the subsequent embodiments and modifications.

Hereinafter, the structural elements mentioned in the above will be described in detail.

Each of the rollers 3 is attached to the inside of the housing 2. Each of the rollers 3 is a rod member that extends horizontally and is formed into a cylindrical shape. Each of the rollers 3 is attached to the inside of the housing 2 with the horizontally extending shaft member 30 intervening therebetween. The shafts 30 are respectively the central axes of the rollers 3. Each of the shafts 30 is coupled to a driving device such as a motor. By the driving device driving, each of the rollers 3 rotates about the shaft member 30 with respect to the housing 2. At this time, one roller 3 rotates in the direction opposite to the direction in which the other roller 3 rotates.

The rollers 3 sandwich the FPD 100 inserted therebetween, thereby holding the FPD 100. At this time, the FPD 100 is held between the rollers 3 while the top face 101 faces upward, the bottom surface 103 faces downward, and the width direction is parallel to the shafts 30 of the rollers 3. The rollers 3 rotate while holding the FPD 100, thereby conveying the held FPD 100 downward at a predetermined speed.

A material that forms the rollers 3 is, for example, rubber. The outer peripheral surfaces of the rollers 3 have adhesiveness. Examples of means for imparting adhesiveness to the outer peripheral surfaces of the rollers 3 include forming the rollers 3 with a highly adhesive material, attaching adhesive sheets to the outer surfaces of the rollers 3, and the like. The rollers 3 convey the FPD 100 wrapped in the first bag 200 downward, and adhere the first bag 200 incised with the side surface incision mechanism 4 and the bottom surface incision mechanism 5 to the outer surface, thereby peeling off the first bag 200 from the FPD 100 and winding up the peeled off first bag 200.

The side surface incision mechanism 4 is fixed to the inner wall of the housing 2. The side surface incision mechanism 4 is disposed slightly above the shafts 30 of the rollers 3. The side surface incision mechanism 4 includes cutters for cutting portions that are included in the first bag 200 and are attached to the side surfaces 102 of the FPD 100. When the FPD 100 to which the first bag 200 is attached is conveyed downward by the rollers 3, the cutters of the side surface incision mechanism 4 respectively move along the Z axis inside the grooves 104 of the side surfaces 102, and portions that are included in the first bag 200 and are attached to the side surfaces 102 are respectively incised by the cutters.

The bottom surface incision mechanism 5 is attached to the inside of the housing 2 while being movable along the X axis below the rollers 3. The bottom surface incision mechanism 5 is connected to a driving device such as a motor. By the driving device driving, the bottom surface incision mechanism 5 moves with respect to the housing 2 along the X axis. By moving with respect to the housing 2 along the X axis, the bottom surface incision mechanism 5 thereby incises a portion that is included in the first bag 200 wrapping the FPD 100 and is attached to the bottom surface 103 of the FPD 100. The bottom surface incision mechanism 5 is normally stored in a retracted position, and moves from the retracted position to the lower side of the rollers 3 only when in use. For example, in a case where the length of the housing 2 in the X axis direction is sufficiently larger than the length of the rollers 3, the retracted position is disposed at the end of the housing 2 in the X axis direction.

As an example, the configuration of the bottom surface incision mechanism 5 having an L-shaped arm will be described. In this configuration example, the bottom surface incision mechanism 5 includes a rail fixed to the inner wall of the housing 2, an L-shaped arm that is movable on the rail by a motor driving, and a cutter attached to a distal end of the L-shaped arm. The rail extends along the X axis. Furthermore, the L-shaped arm includes a first rod member having a proximal end attached to the rail and extending along the Y axis, and a second rod member extending upward from the distal end of the first rod member. Then, a cutter for incising the first bag 200 attached to the FPD 100 is attached to the upper end of the second rod member. When the L-shaped arm moves on the rail, the cutter moves inside the groove 105 of the bottom surface 103 along the X axis, and a portion that is included in the first bag 200 wrapping the FPD 100 and is attached to the bottom surface 103 is incised by the cutter.

The wrapping mechanism 6 is fixed to the inside of the housing 2. The wrapping mechanism 6 is disposed below the rollers 3. The wrapping mechanism 6 includes a fixing mechanism and a sealing mechanism. The fixing mechanism fixes the second bag 300 to the lower side of the rollers 3 in a state where the opening is opened toward a gap between the rollers 3 positioned above. For example, the fixing mechanism may fix the second bag 300 by holding the opening of the second bag 300. The fixing mechanism may be referred to as a fixer.

The sealing mechanism seals the opening of the second bag 300 into which the FPD 100 is inserted. For example, the sealing mechanism seals the opening of the second bag 300 by pressing the opening from both sides while applying heat thereto. The sealing mechanism may be referred to as a sealer.

The take-out port 8 is provided below the rollers 3 and the wrapping mechanism 6. The take-out port 8 includes an opening/closing port that is opened/closed in accordance with an operator's operation. When the opening/closing port is opened with respect to the housing 2, the FPD 100 can be taken out from the inside of the housing 2.

A guide that controls the posture of the FPD 100 may be provided between the pair of rollers 3 and the wrapping mechanism 6 and between the wrapping mechanism 6 and the take-out port 8. The guide is, for example, a roller. In a case where the guide is provided, the conveyance stability of the FPD 100 inside the housing 2 is improved.

Next, an operation of the wrap replacing apparatus 1 according to the present embodiment will be described with reference to FIG. 6 to FIG. 9.

In a case where the first bag 200 that wraps the FPD 100 is replaced with the second bag 300 by using the wrap replacing apparatus 1, an operator first inserts between the rollers 3 in a pair of rollers 3 the FPD 100 wrapped in the first bag 200. FIG. 6 is a diagram showing a state in which the FPD 100 wrapped in the first bag 200 is inserted between the rollers 3. The inserted FPD 100 is sandwiched between the rollers 3 and fixed therebetween.

Next, by operating an operation button (not shown), etc., an operator inputs an operation to start replacement of a bag that wraps the FPD 100. When the operation to start replacement of a bag that wraps the FPD 100 is input, the wrap replacing apparatus 1 first drives the driving device connected to the bottom surface incision mechanism 5, thereby moving the bottom surface incision mechanism 5 along the X axis slightly below the FPD 100 installed between the rollers 3. At this time, by the cutter of the bottom surface incision mechanism 5 moving along the groove 105 provided in the bottom surface 103 of the FPD 100, a portion that is included in the first bag 200 and is attached to the bottom surface 103 is incised.

After the incision of the first bag 200 attached to the bottom surface 103 is completed, the wrap replacing apparatus 1 rotates the rollers 3 by driving the driving device connected to each of the rollers 3, thereby conveying downward the FPD 100 held between the rollers 3. FIG. 7 is a diagram showing a state in which the FPD 100 held between the rollers 3 is conveyed downward. At this time, by the cutters of the side surface incision mechanism 4 respectively moving along the grooves 104 provided in the side surfaces 102 of the FPD 100, in the first bag 200, the portion attached to the side surfaces 102 is incised. The first bag 200 incised by the side surface incision mechanism 4 and the bottom surface incision mechanism 5 adheres to the outer surfaces of the rollers 3 due to their adhesiveness. When the rollers 3 rotate in a state in which the incised first bag 200 is adhered to the outer surfaces of the rollers 3, the FPD 100 is conveyed downward, and at the same time, the first bag 200 is peeled off from the FPD 100. Then the incised first bag 200 is wound around each of the rollers 3. The FPD 100 from which the first bag 200 has been peeled off is inserted into the inside of the second bag 300 fixed to the fixing mechanism of the wrapping mechanism 6.

When the FPD 100 is inserted into the inside of the second bag 300, the wrap replacing apparatus 1 drives the driving device connected to the sealing mechanism, thereby sealing the opening of the second bag 300 into which the FPD 100 is inserted. FIG. 8 is a diagram showing a state in which the opening of the second bag 300 is sealed. By sealing the opening of the second bag 300, the FPD 100 from which the first bag 200 has been peeled off is wrapped in the second bag 300.

Figure 9:
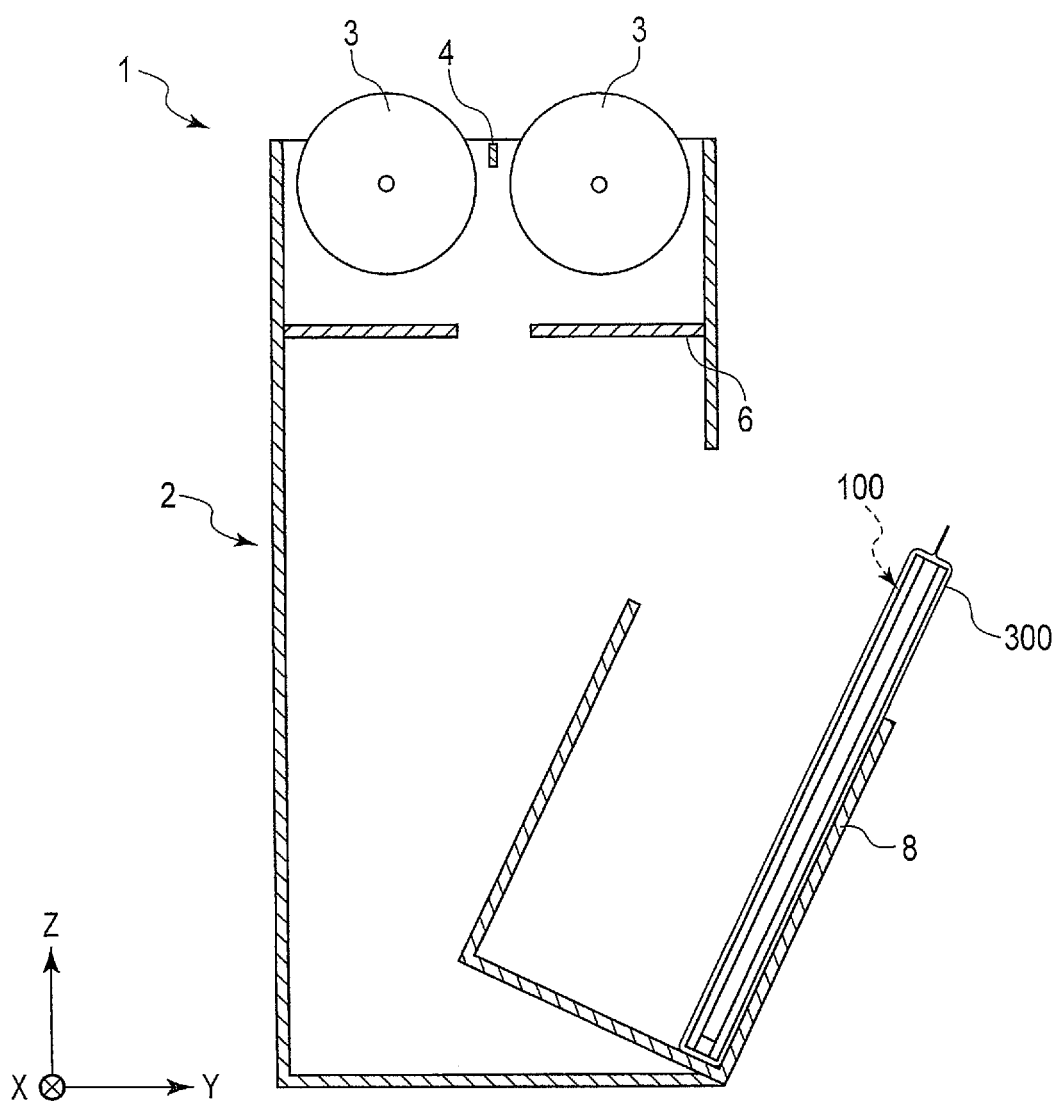
FIG. 9 is a diagram showing a state in which a take-out port of the wrap replacing apparatus according to the first embodiment is opened.

When the FPD 100 is wrapped in the second bag 300, the wrap replacing apparatus 1 conveys the FPD 100 wrapped in the second bag 300 to the take-out port 8. By opening the take-out port 8, the operator can take out the FPD 100 wrapped in the second bag 300 from the inside of the housing 2 to the outside. FIG. 9 is a diagram showing a state in which the take-out port 8 is open. After replacing gloves that have touched the first bag 200, the operator takes out the FPD 100 wrapped in the second bag 300 from the take-out port 8.

When the FPD 100 wrapped in the second bag 300 is taken out, the operator peels off the wound first bag 200 from each of the rollers 3 and collects it in preparation for the next replacement of the bag with respect to the FPD 100. Thereafter, a new second bag 300 is installed in the wrapping mechanism 6.

Hereinafter, the advantageous effects of the wrap replacing apparatus 1 according to the present embodiment will be described.

The wrap replacing apparatus 1 according to the present embodiment includes a peeler for peeling off the first bag 200 from the FPD 100 wrapped in the first bag 200, and the wrapping mechanism 6 for wrapping, in the second bag 300, the FPD 100 from which the first bag 200 has been peeled off.

With the configuration described in the above, the peeler peels off the first bag 200 from the FPD 100, and the wrapping mechanism 6 wraps the FPD 100 in the second bag 300, so that an infection prevention bag configured to wrap the FPD 100 can easily be replaced. That is, with the wrap replacing apparatus 1 according to the present embodiment, the infection prevention bag that wraps the X-ray detector can be replaced automatically and easily. Therefore, the operator can replace the bag that wraps the X-ray detector without anxiety.

Furthermore, it is not necessary to replace the bag while holding the FPD 100. Thus, the FPD 100 wrapped in the second bag 300 can be taken out after the gloves that have held the first bag 200 are replaced. Accordingly, replacement operation of the bag that wraps the FPD 100 can be performed by one person. In addition, the number of bags that wrap the FPD 100 can be set to one.

The wrap replacing apparatus 1 further includes an insertion port into which the FPD 100 is inserted and the take-out port 8 from which the FPD 100 wrapped in the second bag 300 is taken out. The insertion port is provided at a position in which the rollers 3 are disposed. The take-out port 8 is provided at a position different from the insertion port.

With the configuration described in the above, the FPD 100 wrapped in the second bag 300 can be taken out at a position different from the insertion port into which the first bag 200 is inserted. This surely prevents bacteria and viruses adhering to the first bag 200 from adhering to the second bag 300 attached to the FPD 100.

Furthermore, the peeler includes the pair of rollers 3 that sandwich and hold the FPD 100 wrapped in the first bag 200. The pair of rollers 3 convey the FPD 100 wrapped in the first bag 200 by rotating while holding the FPD 100 wrapped in the first bag 200.

With the configuration described in the above, the FPD 100 can be held between the rollers 3. Furthermore, by causing the roller 3 to rotate while holding the FPD 100, the FPD 100 can be automatically conveyed to the inside of the housing 2 at a predetermined speed.

Furthermore, the wrap replacing apparatus 1 further includes an inciser for cutting the first bag 200 that wraps the FPD 100 along the groove provided in the FPD 100.

The inciser includes the bottom surface incision mechanism 5 and the side surface incision mechanism 4. The bottom surface incision mechanism 5 moves inside the groove 105 provided in the bottom surface 103 of the FPD 100, thereby incising a portion that is included in the first bag 200 and is attached to the bottom surface 103 of the FPD 100. The side surface incision mechanism 4 is fixed to the upper side of the shafts 30 of the rollers 3, and incises the portions that are included in the first bag 200 and are respectively attached to the side surfaces 102 of the FPD 100 by being conveyed downward by the rollers 3 in a state in which the side surface incision mechanism 4 is disposed inside each of the grooves 104 provided in the side surfaces 102 of the FPD 100.

With the wrap replacing apparatus 1 according to the present embodiment having the configuration described in the above, when the FPD 100 wrapped in the first bag 200 used for the X-ray inspection is set between the rollers 3, by activation of the bottom surface incision mechanism 5, the first bag 200 attached to the bottom surface 103 of the FPD 100 can be automatically incised. Thereafter, by the rollers 3 rotating, the FPD 100 is automatically conveyed to the inside of the housing 2. At this time, with the side surface incision mechanism 4, the first bag 200 attached to each of the side surfaces 102 of the FPD 100 can be automatically incised.

Furthermore, the outer peripheral surfaces of the rollers 3 have adhesiveness. The FPD 100 is conveyed downward with the rollers 3, and the first bag 200 peeled off from the FPD 100 is wound around each of the rollers 3.

With the above configuration, by the rollers 3 rotating in a state in which the infection prevention bag that wraps the FPD 100 is adhered to the surfaces of the rollers 3, the infection prevention bag can be efficiently peeled off from the FPD 100 and the peeled off bag can be efficiently wound up.

Modification of First Embodiment

Each of the rollers 3 may be disposable. For example, every time bag replacement is performed on a single FPD 100, the roller 3 around which the first bag 200 wound may be discarded and replaced with a new roller 3. In this case, since the peeled off first bag 200 can be discarded together with the roller 3, the load of peeling off the first bag 200 wound around the roller 3 from the roller 3 can be eliminated. Furthermore, this configuration is preferable in terms of hygiene, too, because the peeled off first bag 200 can be discarded without directly touching it.

Second Embodiment

Next, the second embodiment will be described. The present embodiment corresponds to the first embodiment modified in configuration as will be described below. Descriptions of the configurations, operations, and advantageous effects similar to those of the first embodiment will be omitted.

In the wrap replacing apparatus 1 according to the present embodiment, instead of imparting adhesiveness to the rollers 3, the rollers 3 are provided with protruding units 35, and the first bag 200 is provided with engagement units 210 configured to engage with the protruding units 35. By the FPD 100 wrapped in the first bag 200 being disposed between the rollers 3, and by the rollers 3 rotating in a state in which the engagement units 210 are engaged with the protruding units 35, the FPD 100 is conveyed and the first bag 200 peeled off from the FPD 100 is wound around each of the rollers 3. The protruding units 35 may be referred to as a protrusion. The engagement units 210 may be referred to as an engager.

Figure 10:
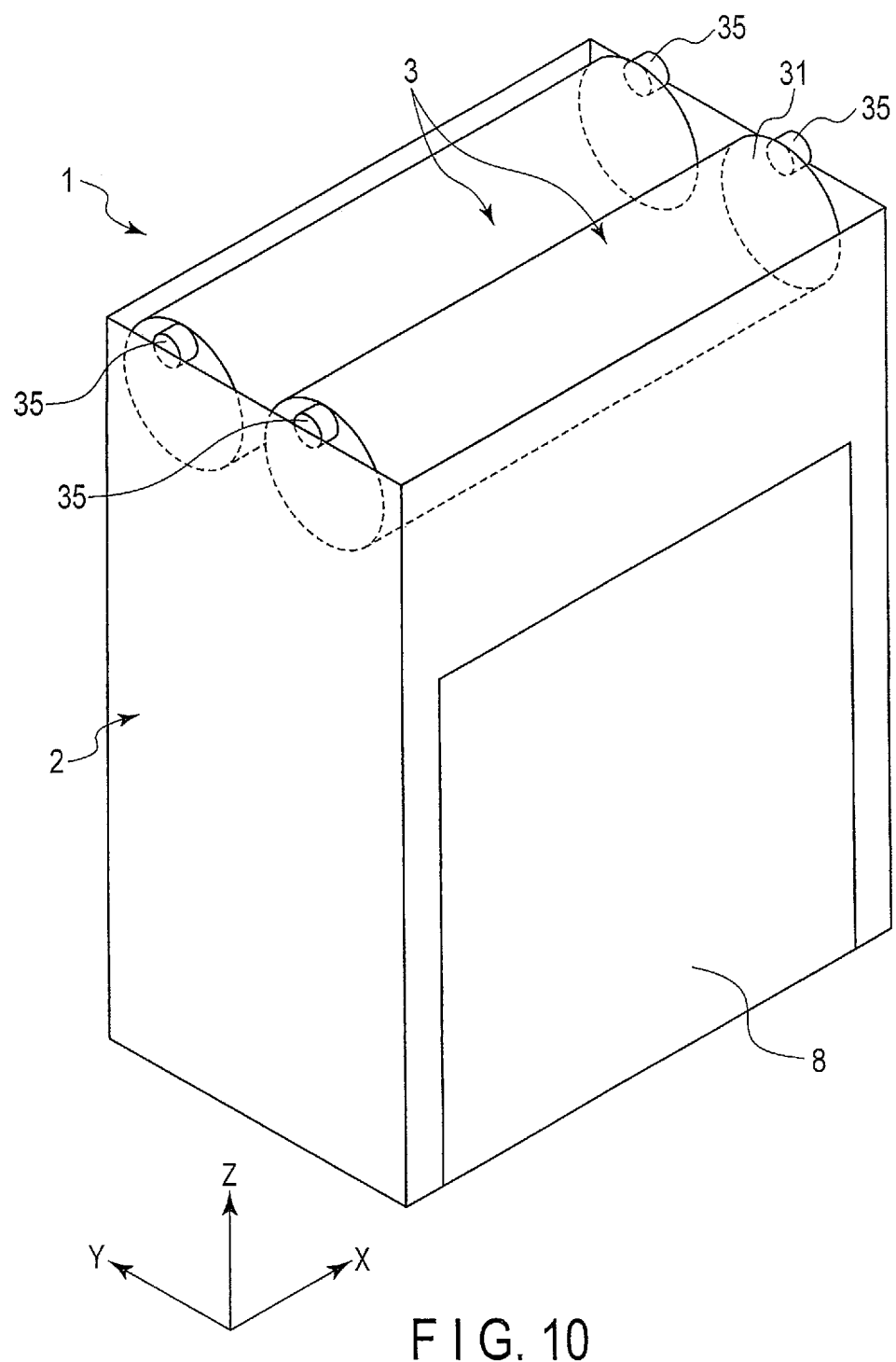
FIG. 10 is a diagram showing a configuration of a wrap replacing apparatus according to a second embodiment.

FIG. 10 is a diagram showing a configuration of the wrap replacing apparatus 1 according to the present embodiment. As shown in FIG. 10, each of the rollers 3 includes a cylindrical unit 31 and two protruding units 35. The cylindrical unit 31 is a rotating body formed into a cylindrical shape extending along the X axis direction. Each of the protruding units 35 protrudes outward from each end surface in the X direction. The protruding units 35 are respectively provided in positions away from the shafts 30 in a cross section perpendicular to the X axis. By the rollers 3 rotating, the protruding units 35 rotate around the shafts 30, respectively.

Hereinafter, the configuration of bags used in the present embodiment will be described with reference to FIG. 11. The first bag 200 will be described as an example with reference to FIG. 11. The second bag 300 has a similar configuration to that of the first bag 200.

Figure 11:
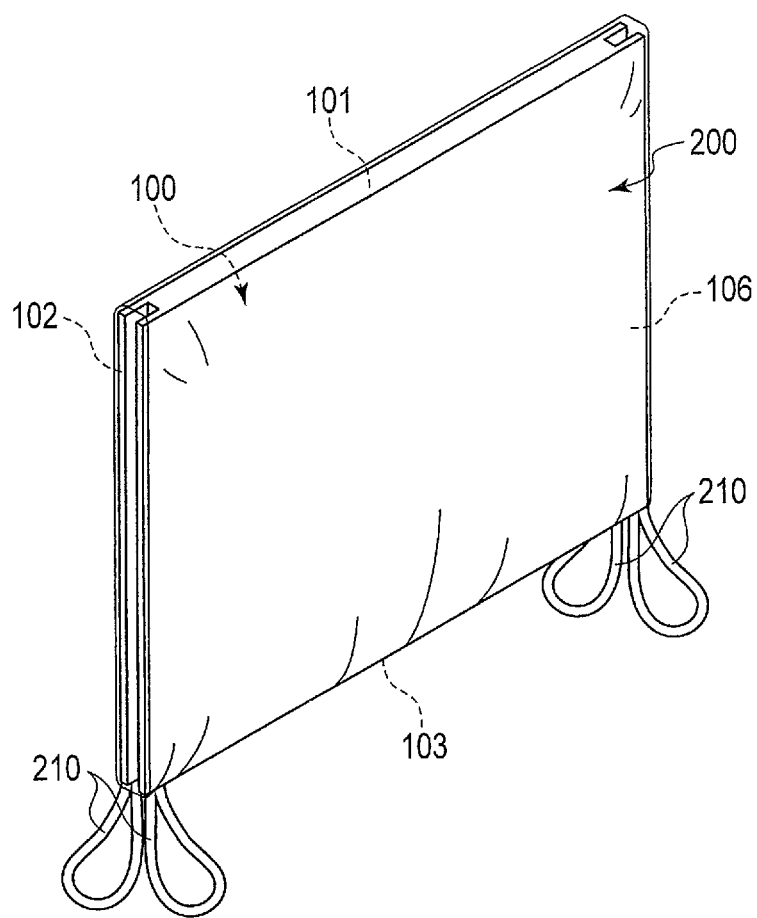
FIG. 11 is a diagram showing a state in which an X-ray detector that uses the wrap replacing apparatus according to the second embodiment is wrapped in a first bag.

FIG. 11 is a diagram showing a state in which the FPD 100 used in the wrap replacing apparatus 1 according to the present embodiment is wrapped in the first bag 200. As shown in FIG. 11, the first bag 200 is provided with the plurality of engagement units 210.

Each of the engagement units 210 is a ring-shaped hook. The engagement units 210 are respectively attached to portions of the first bag 200, which respectively come into contact with the four corners of the bottom surface 103 when the first bag 200 is attached to the FPD 100. The engagement units 210 are made from the same material as that of the first bag 200. The engagement units 210 may be made from a resin material.

Each of the engagement units 210 is formed into a shape that enables engagement with one of the protruding units 35 of the rollers 3. The engagement units 210 are each formed into a ring shape slightly larger in diameter than the protruding units 35.

It suffices that each of the rollers 3 is provided with one or more protruding units 35. In the present embodiment, each of the rollers 3 in a pair of rollers 3 is provided with two protruding units 35. Therefore, in the present embodiment, four protruding units 35 in total are provided. The first bag 200 is provided with the same number of engagement units 210 as the total number of protruding units 35. Therefore, in the present embodiment, four engagement units 210 in total are provided. The number of engagement units 210 may be smaller than the total number of protruding units 35 or may be greater than the total number of protruding units 35.

Each protruding unit 35 and each engagement unit 210 may take any shape as long as they can engaged with each other. Furthermore, each protruding unit may be provided in the first bag 200, and each engagement unit in a ring shape that engages with each protruding unit may be provided in each roller 3.

Next, an operation of the wrap replacing apparatus 1 according to the present embodiment will be described with reference to FIG. 12.

In a case where the first bag 200 that wraps the FPD 100 is replaced with the second bag 300 by using the wrap replacing apparatus 1, an operator first inserts the FPD 100 wrapped in the first bag 200 between the pair of rollers 3 and fixes the FPD 100 between the rollers 3. FIG. 12 is a diagram showing a state in which the FPD 100 wrapped in the first bag 200 is inserted between the rollers 3. At this time, an operator hooks each of the engagement units 210 attached to the first bag 200 to a corresponding one of the protruding units 35. In this manner, the engagement units 210 respectively engage with the protruding units 35.

Next, by operating an operation button (not shown), etc., the operator inputs an operation to start replacement of the bag wrapping the FPD 100. When the operation to start replacement of the bag wrapping the FPD 100 is input, as with the first embodiment, the wrap replacing apparatus 1 incises a portion that is included in the first bag 200 and is attached to the bottom surface 103 by moving the cutter of the bottom surface incision mechanism 5 along the groove 105 provided in the bottom surface 103 of the FPD 100. Thereafter, the wrap replacing apparatus 1 causes the rollers 3 to rotate. In this manner, by the cutters of the side surface incision mechanism 4 respectively moving along the grooves 104, the portions that are included in the first bag 200 and are attached to the side surfaces 102 are incised.

In the present embodiment, the engagement units 210 of the first bag 200 engage with the protruding units 35 of the rollers 3. Thus, when the FPD 100 is conveyed downward, the first bag 200 incised by the side surface incision mechanism 4 and the bottom surface incision mechanism 5 is pulled by each of the rollers 3. The first bag 200 is peeled off from the FPD 100 and is then wound around each of the rollers 3.

As with the first embodiment, the FPD 100 from which the first bag 200 has been peeled off is wrapped in the second bag 300 by the wrapping mechanism 6, and is then taken out from the take-out port 8.

Hereinafter, the advantageous effects of the wrap replacing apparatus 1 according to the present embodiment will be described.

In the wrap replacing apparatus 1 according to the present embodiment, the rollers 3 include the protruding units 35, and the first bag 200 includes the engagement units 210 that can engage with the protruding units 35. By the rollers 3 rotating in a state in which the engagement units 210 are engaged with the protruding units 35, the FPD 100 is conveyed while the first bag 200 peeled off from the FPD 100 is wound around each of the rollers 3.

With the wrap replacing apparatus 1 according to the present embodiment having the configuration described in the above, the FPD 100 is conveyed in a state in which the protruding unit 35 respectively engages with the engagement units 210. Thus, the first bag 200 incised by the side surface incision mechanism 4 and the bottom surface incision mechanism 5 is pulled by each of the rollers 3, thereby being peeled off from the FPD 100 and being wound around each of the rollers 3. Therefore, as with the first embodiment, in the present embodiment also, the first bag 200 can be automatically peeled off from the FPD 100. In this manner, the infection prevention bag that wraps the X-ray detector can be replaced automatically and easily.

Modification of Second Embodiment

Hereinafter, the modification of the protruding units 35 provided in the rollers 3 will be described with reference to FIG. 13 to FIG. 18.

Figure 13:
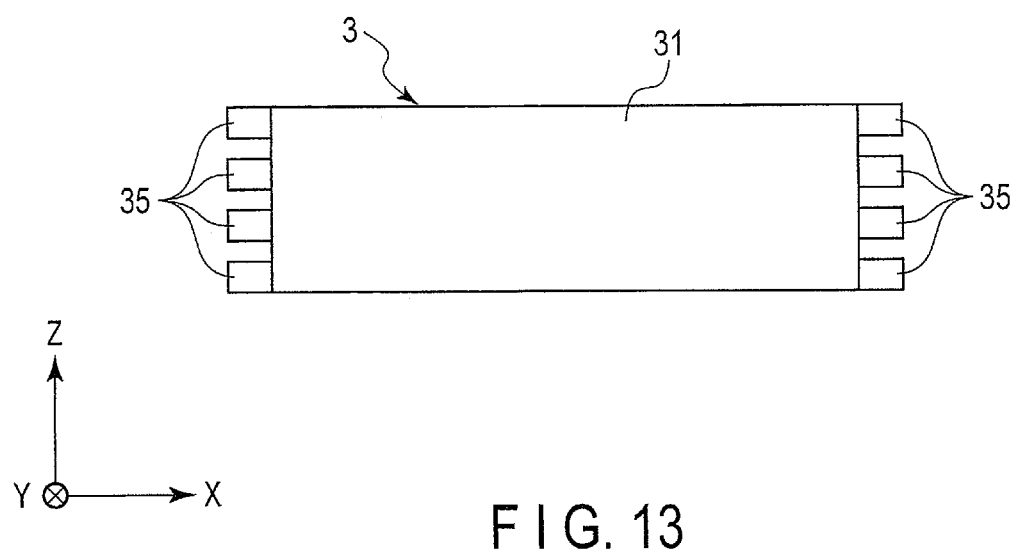
FIG. 13 is a diagram showing an exemplary configuration of rollers according to a modification of the second embodiment.
Figure 14:
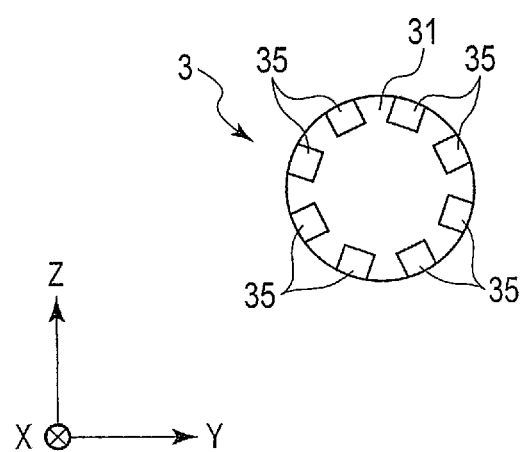
FIG. 14 is a diagram showing the roller shown in FIG. 13 as viewed from one side in a direction along a central axis of the roller.

FIG. 13 and FIG. 14 are each a diagram showing a configuration of each roller 3 in one modification. FIG. 13 is a diagram showing the roller 3 as viewed from one side in the Y axis direction. FIG. 14 is a diagram showing the roller 3 as viewed from one side in the X axis direction. As shown in FIG. 13 and FIG. 14, in this modification, the plurality of protruding units 35 are provided in each end surface of the cylindrical unit 31. The protruding units 35 are provided in positions away from the shafts 30, respectively. The protruding units 35 are disposed at equal intervals along the outer edge of each end surface of the cylindrical unit 31.

Figure 15:
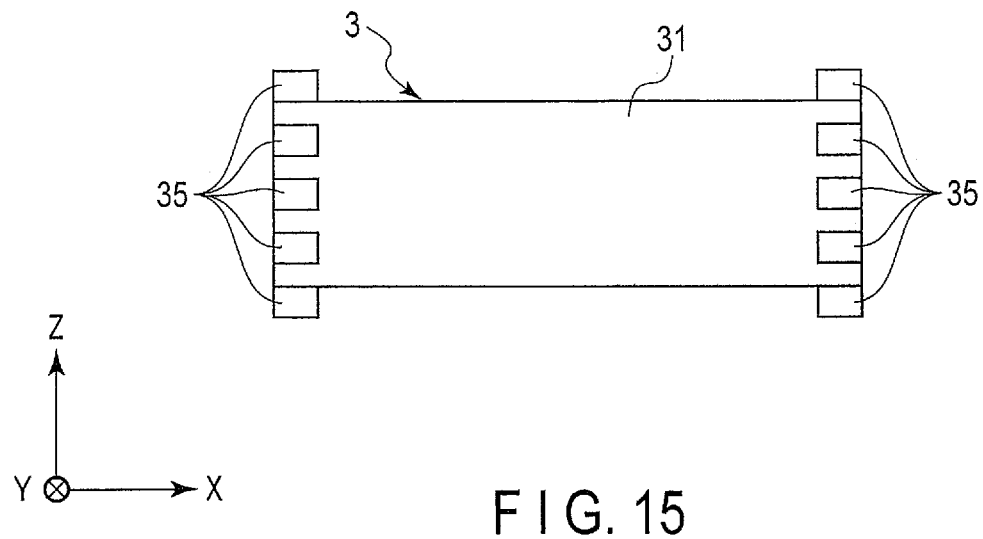
FIG. 15 is a diagram showing an exemplary configuration of the roller according to the modification of the second embodiment.
Figure 16:
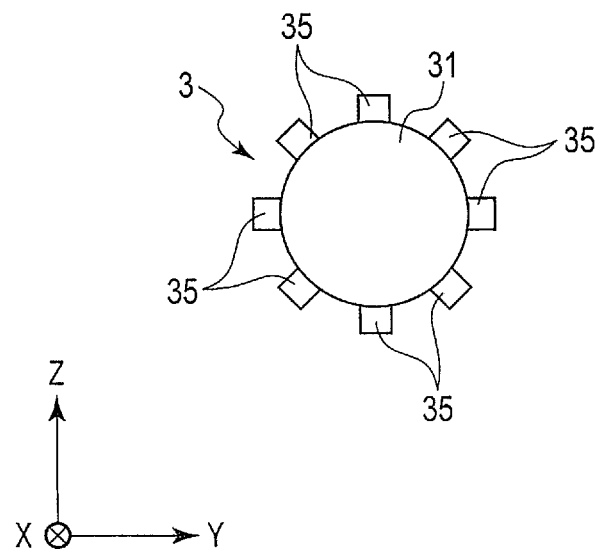
FIG. 16 is a diagram showing the roller shown in FIG. 15 as viewed from one side in the direction along the central axis of the roller.

FIG. 15 and FIG. 16 are each a diagram showing a configuration of each roller 3 in another modification. FIG. 15 is a diagram showing the roller 3 as viewed from one side in the Y axis direction. FIG. 16 is a diagram showing the roller 3 as viewed from one side in the X axis direction. As shown in FIG. 15 and FIG. 16, in this modification, the plurality of protruding units 35 are provided in the outer peripheral surface of each roller 3. The protruding units 35 are disposed in both ends of the cylindrical unit 31 and protrude from the outer peripheral surface of the cylindrical unit 31 in the direction away from the shaft member 30. In each end of the cylindrical unit 31, the protruding units 35 are disposed at equal intervals along the circumferential direction of the cylindrical unit 31.

Figure 17:
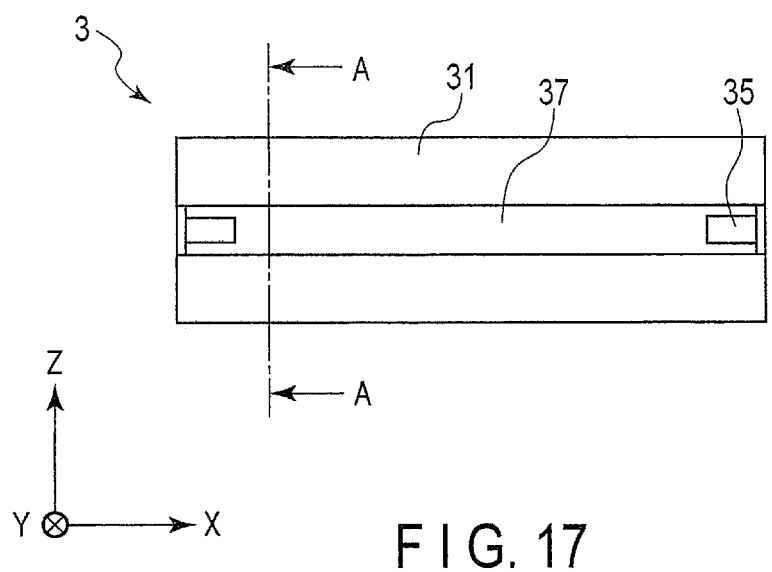
FIG. 17 is a diagram showing an exemplary configuration of the rollers according to the modification of the second embodiment.
Figure 18:
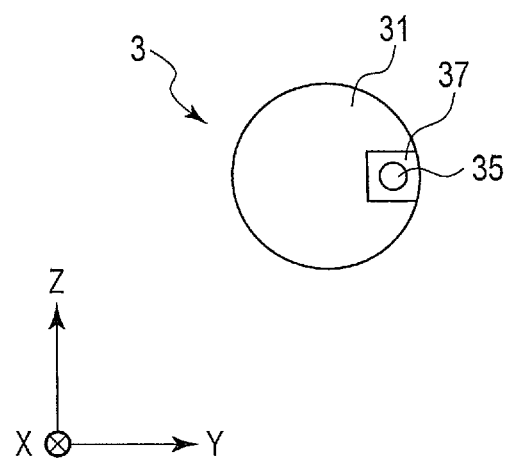
FIG. 18 is a cross-sectional view taken along the line A-A of FIG. 17.

FIG. 17 and FIG. 18 are each a diagram showing a configuration of each roller 3 in another modification. FIG. 17 is a diagram showing the roller 3 as viewed from one side in the Y axis direction. FIG. 18 is a cross-sectional view taken along the line A-A of FIG. 17. As shown in FIG. 17 and FIG. 18, in this modification, a groove 37 recessed toward the shaft member 30 is provided in the outer peripheral surface of each roller 3. The groove 37 extends in the X axis direction of each roller 3.

Two protruding units 35 are provided inside the groove 37. Each of the protruding units 35 protrudes from the surface facing inward in the X axis direction inside the groove 37 to the inside in the X axis direction.

Figure 19:
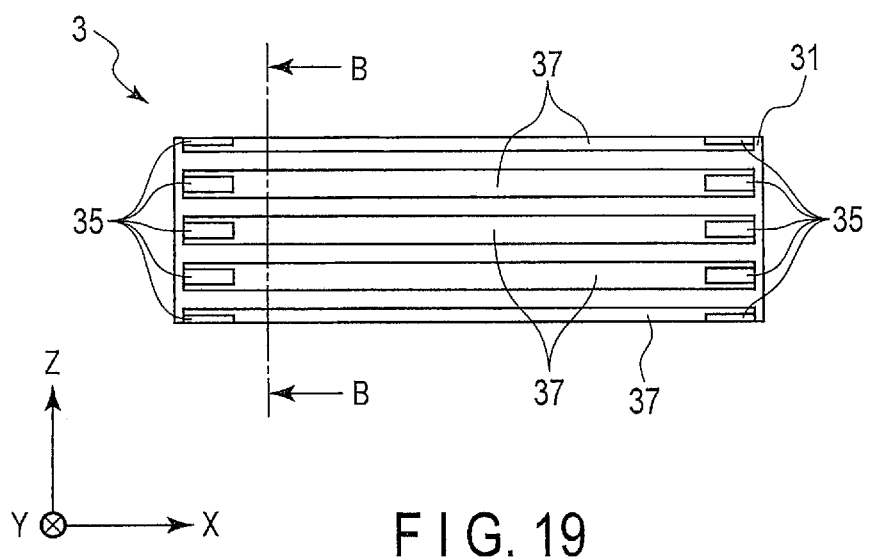
FIG. 19 is a diagram showing an exemplary configuration of the rollers according to the modification of the second embodiment.
Figure 20:
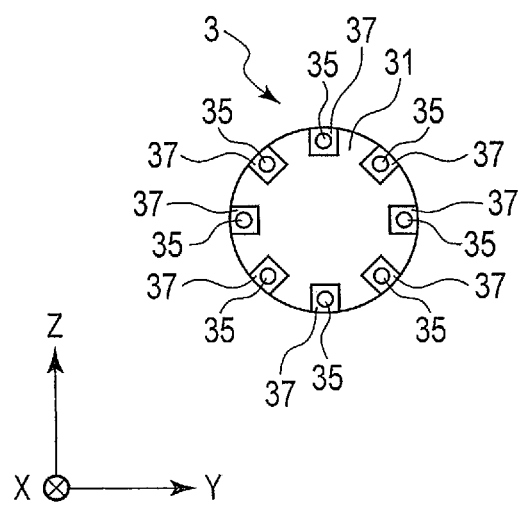
FIG. 20 is a cross-sectional view taken along the line B-B of FIG. 19.

FIG. 19 and FIG. 20 are each a diagram showing a configuration of each roller 3 in another modification. FIG. 19 is a diagram showing the roller 3 as viewed from one side in the Y axis direction. FIG. 20 is a cross-sectional view taken along the line B-B of FIG. 19. As shown in FIG. 19 and FIG. 20, in this modification, a plurality of grooves 37 described with reference to FIG. 17 and FIG. 18 are provided. Each of the grooves 37 extends in the X axis direction. The protruding units 35 are disposed at equal intervals along the circumferential direction of the cylindrical unit 31.

The inside of each protruding unit 37 is provided with two protruding units 35. Each of the protruding units 35 protrudes from the surface facing inward in the X axis direction inside the groove 37 toward the inside in the X axis direction. The groove 37 are disposed at equal intervals along the circumferential direction of the cylindrical unit 31.

In the modifications shown in FIG. 13 to FIG. 20, it is preferable to provide the same number of engagement units 210 as the total number of the protruding units 35 provided in the pair of rollers 3. By the engagement units 210 respectively engaging with the protruding units 35, a force by which the rollers 3 pull the first bag 200 incised by the side surface incision mechanism 4 and the bottom surface incision mechanism 5 increases, so that the first bag 200 can be peeled off from the FPD 100 more surely.

In the modifications shown in FIG. 17 to FIG. 20, the protruding units 35 are provided inside the groove 37 or the grooves 37 provided in the outer peripheral surface of each cylindrical unit 31. In this case, as with the modifications shown in FIG. 13 to FIG. 16, the outer diameter of each roller 3 can be made smaller as compared with the case in which the protruding units 35 protrude outward from the outer peripheral surface of the cylindrical unit 31.

Third Embodiment

Next, the third embodiment will be described. The present embodiment corresponds to the first embodiment modified in configuration as will be described below. Descriptions of the configurations, operations, and advantageous effects similar to those of the first embodiment will be omitted. Instead of imparting adhesiveness to the rollers 3, the wrap replacing apparatus 1 according to the present embodiment includes rotation pins 91 that are provided below each roller 3 and hook to peel off, by rotating, the first bag 200 attached to the FPD 100.

Figure 22:
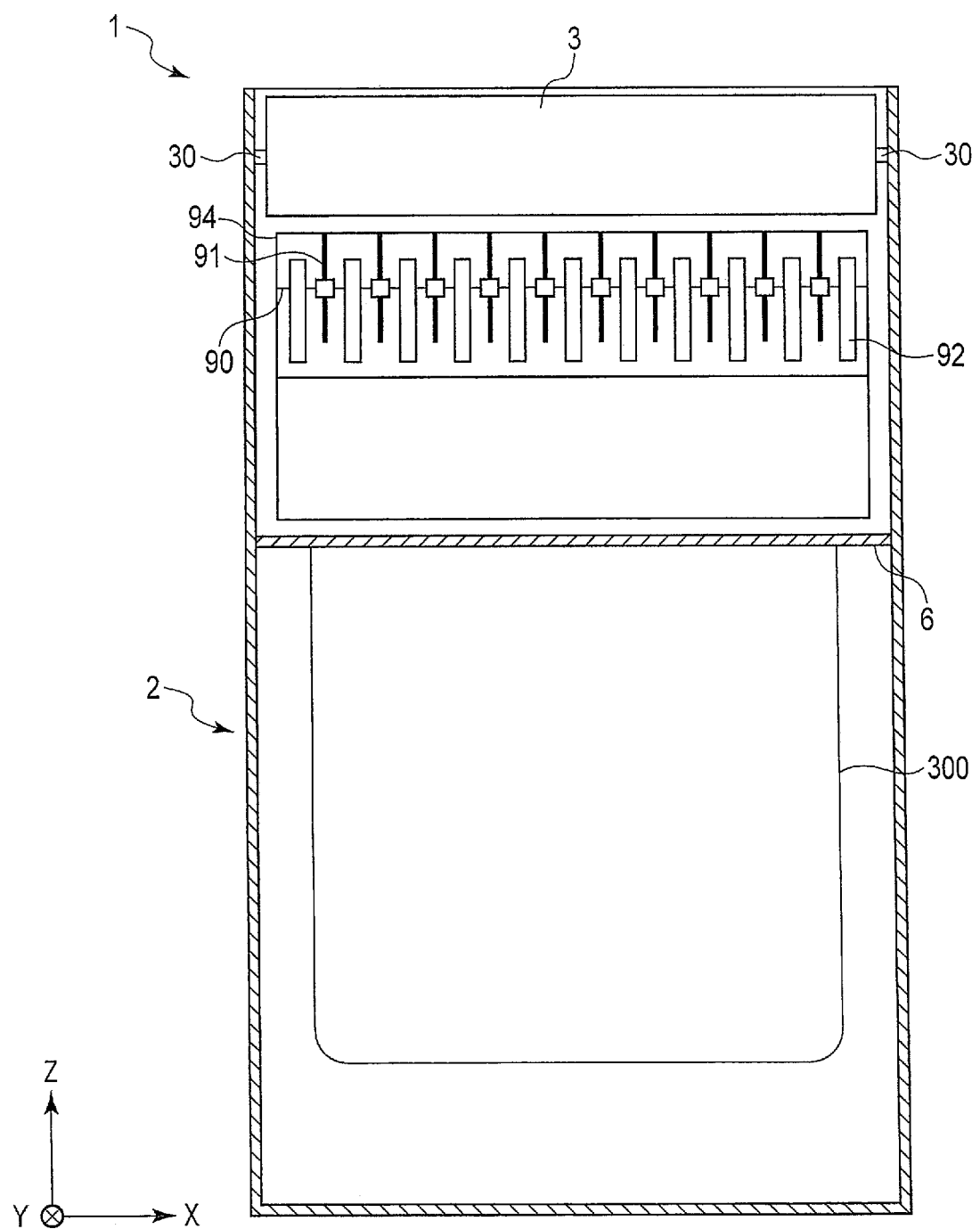
FIG. 22 is a diagram showing an internal configuration of the wrap replacing apparatus according to the third embodiment.

FIG. 21 and FIG. 22 are each a diagram showing a configuration of the wrap replacing apparatus 1 according to the present embodiment. FIG. 21 is a diagram showing the internal configuration of the wrap replacing apparatus 1 in a cross section perpendicular to the X axis. FIG. 22 is a diagram showing the internal configuration of the wrap replacing apparatus 1 as viewed from one side in the X axis direction. As shown in FIG. 21 and FIG. 22, the wrap replacing apparatus 1 includes a pair of shafts 90, a plurality of rotation pins 91, a plurality of first guides 92, a pair of collecting units 93, and a pair of second guides 94. The rotation pins 91, the first guides 92, the collecting units 93, and the second guides 94 are disposed below the rollers 3 and above the wrapping mechanism 6 inside the housing 2.

The shafts 90 are respectively disposed below the rollers 3. The shafts 90 are rod members that extend in parallel to the shafts 30 of the rollers 3, respectively. The shafts 90 are rotatable with respect to the housing 2.

The plurality of rotation pins 91 and the plurality of first guides 92 are attached alternatively to each of the shafts 90. The first guides 92 are disposed at equal intervals along the X axis direction. Each of the rotation pins 91 is disposed between two adjacent first guides 92. The rotation pins 91 are disposed at equal intervals in the X axis direction.

By the shaft member 90 rotating with respect to the housing 2, each of the rotation pins 91 rotates together with the shaft member 90 around the shaft member 90. The first guide unit 92 is attached to the shaft member 90 in a state in which rotation of the first guide unit 92 with respect to the housing 2 is regulated and rotation thereof with respect to the shaft member 90 is allowed. Therefore, even when the shaft member 90 rotates with respect to the housing 2, the first guide unit 92 does not rotate with respect to the housing 2.

Each of the rotation pins 91 includes a plurality of pins that protrude in the direction away from the shaft member 90. The plurality of pins protrude at equal intervals in the circumferential direction centered on the shaft member 90. The pins are each formed in such a manner as to have a length slightly smaller than a distance between each shaft member 90 and the FPD 100 that is conveyed between the shafts 90 in a pair of rollers 3 in the Y axis direction. That is, the pins are each formed into a shape that can hook the first bag 200 that wraps the FPD 100 conveyed between the shafts 90. The rotation pins 91 are made from a resin material, for example.

Each of the first guides 92 is formed in such a manner as to disengage from the rotation pins 91, the first bag 200 being hooked on the rotation pins 91 on the side opposite to the direction in which the FPD 100 is disposed. The first guides 92 are each adjusted in shape and position in such a manner as to come into contact with the first bag 200 hooked on the pins of the rotation pins 91 outside the shaft member 90 in the Y axis direction. The first guides 92 are each, for example, a plate in an oval shape made from a resin material.

The collecting units 93 are disposed below the shaft member 90. The collecting units 93 are each a box configured to collect the first bag 200 disengaged from the rotation pins 91 by the first guides 92. The collecting units 93 may be referred to as a collector.

The second guides 94 are respectively disposed between the rollers 3 and the collecting units 93. The second guides 94 are respectively disposed outside the rotation pins 91 and the first guides 92 in the Y axis direction. The second guides 94 respectively guide to the collecting units 93, the first bag 200 hooked on the rotation pins 91 or the first bag 200 disengaged from the rotation pins 91 by the first guides 92. The second guides 94 are each, for example, a curved plate extending in the X axis direction.

The wrap replacing apparatus 1 further includes, as an inciser, an upper surface incision mechanism in addition to the side surface incision mechanism 4 and the bottom surface incision mechanism 5. After the first bag 200 is peeled off from the FPD 100, the upper surface incision mechanism incises a portion that is included in the first bag and was attached to the upper surface 101 of the FPD 100.

The upper surface incision mechanism is attached to the inside of the housing 2. The upper surface incision mechanism is connected to a driving device such as a motor, and by the driving device driving, moves along the X axis. The upper surface incision mechanism moves with respect to the housing 2 along the X axis, thereby incising a portion that is included in the first bag 200 wrapping the FPD 100 and was attached to the upper surface 101 of the FPD 100.

The upper surface incision mechanism is implemented by a similar configuration to that of the bottom surface incision mechanism 5. For example, the upper surface incision mechanism includes a rail and an L-shaped arm. The rail is fixed to the inner wall of the housing 2. The L-shaped arm is movable on the rail and has a distal end provided with a down-pointing cutter.

A portion included in the first bag 200 and attached to the upper surface 101 of the FPD 100 may be incised by the upper surface incision mechanism in a state in which rotation of the rollers 3 is suspended during conveyance of the FPD 100 with the rollers 3. In this case, the groove that passes through the cutter of the upper surface incision mechanism is formed across the whole upper surface 101 of the FPD 100 in the width direction.

Next, an operation of the wrap replacing apparatus 1 according to the present embodiment will be described with reference to FIG. 23.

In a case where the first bag 200 that wraps the FPD 100 is replaced with the second bag 300 by using the wrap replacing apparatus 1, an operator first inserts the FPD 100 wrapped in the first bag 200 between the pair of rollers 3 and fixes the FPD 100 between the rollers 3.

Next, by operating an operation button (not shown), etc., the operator inputs an operation to start replacement of the bag wrapping the FPD 100. When the operation to start replacement of the bag wrapping the FPD 100 is input, as with the first embodiment, the wrap replacing apparatus 1 incises a portion that is included in the first bag 200 and is attached to the bottom surface 103 by moving the cutter of the bottom surface incision mechanism 5 along the groove 105 provided in the bottom surface 103 of the FPD 100. Thereafter, the wrap replacing apparatus 1 rotates the rollers 3. In this manner, by the cutters of the side surface incision mechanism 4 respectively moving along the grooves 104, a portion that is included in the first bag 200 and is attached to the side surfaces 102 is incised. FIG. 23 is a diagram showing a state in which the FPD 100 wrapped in the first bag 200 is conveyed by the rollers 3.

In the present embodiment, the wrap replacing apparatus 1 rotates the rollers 3 and at the same time, rotates the shafts 90 in the direction opposite to the rollers 3. In this manner, the FPD 100 is conveyed downward and at the same time, the rotation pins 91 attached to each shaft member 90 hook the first bag 200 incised by the side surface incision mechanism 4 and the bottom surface incision mechanism 5. By the pins of the rotation pins 91 hooking the first bag 200, the first bag 200 is peeled off from the FPD 100. As with the first embodiment, the FPD 100 from which the first bag 200 has been peeled off is wrapped in the second bag 300 by the wrapping mechanism 6, and is then taken out from the take-out port 8.

In the first bag 200 peeled off from the FPD 100 by the rotation pins 91, a portion that was attached to the upper surface 101 of the FPD 100 is incised by the upper surface incision mechanism. The first bag 200 peeled off from the FPD 100 is conveyed outward in the Y axis direction by the rotation pins 91 rotating, and comes into contact with the first guides 92 outside the shafts 90. By the first bag 200 coming into contact with each first guide unit 92, the first bag 200 is disengaged from the rotation pins 91. The first bag 200 disengaged from the rotation pins 91 is guided by each second guide unit 94 to the inside of each collecting unit 93, thereby being collected by each collecting unit 93.

Hereinafter, the advantageous effects of the wrap replacing apparatus 1 according to the present embodiment will be described.

The wrap replacing apparatus 1 according to the present embodiment includes the rotation pins 91 and the collecting units 93. The rotation pins 91 peel off the first bag 200 attached to the FPD 100. The collecting units 93 collect the first bag 200 hooked on the rotation pins 91.

With the wrap replacing apparatus 1 according to the present embodiment having the configuration described in the above, the first bag 200 incised by the side surface incision mechanism 4 and the bottom surface incision mechanism 5 is peeled off from the FPD 100 by the rotation pins 91. The first bag 200 peeled off from the FPD 100 by the rotation pins 91 is collected by the collecting units 93. Therefore, as with the first embodiment, the first bag 200 can be automatically peeled off from the FPD 100 in the present embodiment. In this manner, the infection prevention bag that wraps the X-ray detector can be replaced automatically and easily.

The wrap replacing apparatus 1 according to the present embodiment further includes the upper surface incision mechanism that moves in the width direction of the FPD 100, thereby incising a portion that is included in the first bag 200 and is attached to the upper surface 101 of the FPD 100.

With the wrap replacing apparatus 1 according to the present embodiment having the configuration described in the above, the first bag 200 incised by the side surface incision mechanism 4 and the bottom surface incision mechanism 5 is further incised by the upper surface incision mechanism, so that all portions of the first bag 200 can be collected by the collecting units 93. Accordingly, replacement of the bag with respect to the plurality of FPDs 100 can be continuously performed without collecting the first bag 200 peeled off from the FPD 100 every time replacement of the bag is performed on the FPD 100. This further facilitates replacement operation of the infection prevention bag that wraps the FPD 100.

Modification of Third Embodiment

In order to effectively house the first bag 200 that is conveyed to the collecting units 93, each of the collecting units 93 may be provided with a folding mechanism that automatically folds the first bag 200. The folding mechanism is implemented by a plate-like member that rotates inside the collecting unit 93. In this case, the plate-like member is disposed in the vicinity of the outer wall surface of each collecting unit 93 in the Y axis direction. The plate-like member, in which one side in parallel to the Y axis direction is connected to the bottom surface of each collecting unit 93, rotates with respect to each collecting unit 93 around a connection portion connected to each collecting unit 93. By the plate-like member rotating inside each collecting unit 93, the plate-like member repeats an operation in which the plate-like member in an upright posture substantially in parallel to the outer wall surface of each collecting unit 93 falls inward in the Y axis direction and an operation in which the plate-like member in a fallen state rises. By repeating the aforementioned operations at certain intervals when the first bag 200 is conveyed to the collecting units 93, the conveyed first bag 200 can be folded automatically and sequentially.

The folding mechanism may be implemented by, instead of the plate-like member described in the above, a U-shaped rod member having both ends rotatably connected to the bottom surface of each collecting unit 93.

Fourth Embodiment

Next, the fourth embodiment will be described. The present embodiment corresponds to the first embodiment modified in configuration as will be described below. Descriptions of the configurations, operations, and advantageous effects similar to those of the first embodiment will be omitted.

FIG. 24 is a diagram showing a configuration of the wrap replacing apparatus 1 according to the present embodiment. The wrap replacing apparatus 1 according to the present embodiment replaces a wrap configured to wrap an ultrasound probe 400 wirelessly connected to an ultrasonic diagnostic apparatus. Specifically, the wrap replacing apparatus 1 is an apparatus that peels off a first bag 500 from the ultrasound probe 400 wrapped in the first bag 500 and automatically wraps the ultrasound probe 400 in a second bag 600 (not shown). The first bag 500 and the second bag 600 are each a sterilized cover configured to wrap the ultrasound probe 400 in order to prevent infection during X-ray examinations performed on patients with infectious diseases such as COVID-19.

The ultrasound probe 400 includes an ultrasonic vibrator that generates ultrasonic waves and a transmission/reception unit that transmits and receives ultrasonic waves to/from a subject. The ultrasound probe 400 includes a configuration that enables data generated by ultrasonic waves to be transmitted/received to/from a subject.

The ultrasound probe 400 includes a distal end surface 401 and a bottom surface 402. The distal end surface 401 is provided with the ultrasonic wave transmission/reception unit. The bottom surface 402 is provided in an end opposite to the distal end surface 401. The ultrasound probe 400 includes a front surface 403 and a back surface 404. In the front surface, a display unit, etc. is disposed. The back surface 404 faces the side opposite to the front surface 403. The front surface 403 and the back surface 404 are provided in parallel to each other along the central axis of the ultrasound probe 400. That is, the ultrasound probe 400 has a certain thickness.

Furthermore, the ultrasound probe 400 includes two side surfaces 405 facing the direction intersecting the distal end surface 401, the bottom surface 402, the front surface 403, and the back surface 404. Part of each side surface 405 has a curved surface. Herein, the direction that is orthogonal to the central axis of the ultrasound probe 400 and is in parallel to the front surface 403 and the back surface 404 is set to the width direction of the ultrasound probe 400. Width W of the ultrasound probe 400 corresponds to a distance between two side surfaces 405. The width W of the ultrasound probe 400 varies depending on a position in the direction along the central axis. The ultrasound probe 400 becomes larger in width W as it extends from a portion to be held by a user toward the distal end side, and then becomes smaller in width W in the distal end portion.

Furthermore, as with the first embodiment, the side surfaces 403 and the bottom surface 402 of the ultrasound probe 400 are each provided with a groove into which the side surface incision mechanism 4 or the bottom surface incision mechanism 5 is inserted.

The ultrasound probe 400 wrapped in the first bag 500 is inserted into the insertion port of the wrap replacing apparatus 1 in a state in which the center axis of the ultrasound probe 400 is coincident with the vertical direction. Herein, a case will be described in which the ultrasound probe 400 is inserted into the insertion port with the distal end surface 401 facing downward. However, the wrap replacing apparatus 1 may be configured in such a manner that the ultrasound probe 400 is inserted with the distal end surface 401 facing upward.

As with the first embodiment, the wrap replacing apparatus 1 includes the housing 2, the pair of rollers 3, the side surface incision mechanism 4 (not shown), the wrapping mechanism 6 (not shown), and the take-out port 8. The wrap replacing apparatus 1 includes, instead of the bottom surface incision mechanism 5, a distal end surface incision mechanism (not shown) configured to incise a portion that is included in the first bag 500 and is attached to the distal end surface of the ultrasound probe 400. The distal end surface incision mechanism has a similar configuration to that of the bottom surface incision mechanism 5. The distal end surface incision mechanism corresponds to the inciser. The pair of rollers 3 correspond to a peeler.

The housing 2, the pair of rollers 3, the side surface incision mechanism 4, the distal end surface incision mechanism, the wrapping mechanism 6, and the take-out port 8 are appropriately adjusted in their arrangement and shape in accordance with the size and shape of the ultrasound probe 400. For example, the distance between the rollers 3 in a pair of rollers 3 provided as the insertion port and the conveyer is set to slightly greater than the thickness of the ultrasound probe 400 because the ultrasound probe 400 to be inserted is sandwiched and conveyed by the rollers 3.

With the wrap replacing apparatus 1 according to the present embodiment having the configuration described in the above, the peeling mechanism peels off the first bag 500 from the ultrasound probe 400, and the wrapping mechanism 6 wraps the ultrasound probe 400 in the second bag 600, so that an infection prevention bag configured to wrap the ultrasound probe 400 can be easily replaced.

Furthermore, as with the ultrasound probe 400 shown in FIG. 24, in the case of the ultrasound probe 400 having a width which is not uniform in the direction along the central axis, it is preferable that the cutters of the side surface incision mechanism 4 be biased from the inner wall of the housing 2 toward the inner side. For example, the inner wall of the housing 2 and the cutters are connected to each other with a spring. In this case, by the cutters moving inside the grooves provided in the side surfaces 405 while being biased toward the inner side, even in the case of the side surfaces 405 each being provided with a curved surface, portions that are included in the first bag 500 and are attached to the side surfaces 405 of the ultrasound probe 400 can be incised. As described in the above, with respect to a medical device whose width is not uniform, such as the ultrasound probe 400, the infection prevention bag that wraps the ultrasound probe 400 can also be replaced easily.

The present embodiment describes the case of replacing the wrap of the ultrasound probe 400 having a uniform thickness; however, the present embodiment is also applicable to the case of replacing the wrap of the ultrasound probe 400 having a thickness which is not uniform in the direction along the central axis. In such a case, one of the rollers 3 in a pair of rollers 3 is biased in the direction toward the other. In this manner, bias is performed in such a manner as to decrease a distance between the rollers 3. The bias is performed on the rollers 3 using, for example, an elastic member such as a spring. When conveying the ultrasound probe 400 inserted between the rollers 3 in a pair of rollers 3, a position of the biased roller 3 is moved while the distance between the rollers 3 in a pair of rollers 3 varies depending on a change in thickness of the inserted ultrasound probe 400. In this manner, the pair of rollers 3 can effectively function as the conveyer with respect to the ultrasound probe 400 whose thickness is not uniform, too.

Modification of First to Fourth Embodiments

Hereinafter, the modification of the first to fourth embodiments will be described. Herein, a case in which the wrap of the FPD 100 is replaced as in the first to third embodiment will be described as an example; however, the same configuration is also applicable to the case in which the wrap of the ultrasound probe 400 is replaced as in the fourth embodiment.

In the bag wrapping the FPD 100, a portion desired to be incised may be provided with a fragile portion smaller in strength than the remaining portion. In the bag wrapping the FPD 100, a portion attached to the side surface 102 and a portion attached to the bottom surface 103 are provided with fragile portions, respectively. The fragile portions are each implemented by, for example, making a portion of the bag thinner than the remaining portion. Alternatively, the fragile portions are each implemented by forming a perforation. In the case of forming the fragile portions described in the above, by the rollers 3 and the rotation pins 91 exerting a force that pulls the first bag 200 to both sides when the FPD 100 wrapped in the first bag 200 is conveyed by the rollers 3, the first bag 200 is automatically incised from the fragile portion. Therefore, in the case of providing the bag wrapping the FPD 100 with the fragile portions, the side surface incision mechanism 4, the bottom surface incision mechanism 5, the upper surface incision mechanism, and the grooves 104 and 105 of the FPD 100 may be omitted.

The second bag 300 may be produced using a heat-shrinkable sheet that shrinks from heat applied thereto. In this case, the wrapping mechanism 6 wraps the FPD 100 from which the first bag 200 is peeled off in a single heat-shrinkable sheet, and thereafter applies heat to the heat-shrinkable sheet, thereby producing the second bag 300 that wraps the FPD 100. Specifically, a single folded heat-shrinkable sheet is installed in the wrapping mechanism 6. When the FPD 100 from which the first bag 200 is peeled off is disposed on the heat-shrinkable sheet, the FPD 100 is wrapped in the heat-shrinkable sheet and then hot air is applied to the heat-shrinkable sheet. By applying hot air, the heat-shrinkable sheet wrapping the FPD 100 shrinks, thereby producing the second bag 300 in such a manner as to wrap the FPD 100. In this case, the FPD 100 can be wrapped in the second bag 300 in such a manner as to prevent air from entering into a gap between the second bag 300 and the FPD 100. Furthermore, since no air enters into a gap between the second bag 300 and the FPD 100, the FPD 100 is easy to hold and is hard to slip off when it is held.

In addition, the rollers around which the heat-shrinkable sheet is wound may be fixed to the inside of the housing 2. In this case, every time replacement of a bag is completed with respect to a single X-ray detector, a new heat-shrinkable sheet is supplied from the rollers to the wrapping mechanism 6. The rollers are one example of a supplier.

The heat-shrinkable sheet may be automatically suppled from the rollers in response to the take-out port 8 being opened. The heat-shrinkable sheet may be automatically suppled from the rollers based on detection of the fact that the FPD 100 has been taken out from the take-out port 8.

The wrap replacing apparatus 1 may be configured in such a manner as to replace only the outer layer of a double-layer bag wrapping the FPD 100. In this case, for example, the wrap replacing apparatus 1 is configured in such a manner that only the outer layer is provided with a fragile portion having a low strength, and only the outer layer is peeled off from the FPD 100 by being pulled by the rollers 3 having adhesiveness. Alternatively, the wrap apparatus 1 may be configured in such a manner that only the outer layer of the double-layer bag is incised by the side surface incision mechanism 4 and the bottom surface incision mechanism 5 by inserting between the two layers of the double-layer bag wrapping the FPD 100 a blocking plate for preventing the side surface incision mechanism 4 and the bottom surface incision mechanism 5 from incising the inner layer of the double-layer bag.

In the embodiments described in the above, as an example, the case in which the grooves are formed in the side surface of the FPD is described. However, the embodiments can be implemented using a general FPD in which no grooves are formed in the side surfaces. This case may use an attachment which is formed in a detachably attachable manner to each of the side surfaces of the FPD and has a groove provided in an outer side. For example, the FPD may be wrapped in a plastic bag in a state in which the attachment is attached to each side surface of the FPD. The FPD wrapped in the plastic bag is inserted into the wrap replacing apparatus 1 and is conveyed. When the FPD is conveyed in the wrap replacing apparatus 1, the groove formed in the attachment is provided in such a manner as to come into contact with a cutter provided to the side surface incision mechanism 4 or the bottom surface incision mechanism 5 of the wrap replacing apparatus 1. According to the wrap replacing apparatus 1 and the FPD thus configured, the FPD is inserted into the wrap replacing apparatus 1 and is conveyed therethrough, and the cutter of the incision mechanism comes into contact with the groove formed in the attachment. In this manner, the plastic bag in which the FPD positioned between the cutter and the groove is wrapped is incised. Furthermore, the attachment may also be used in the case in which the FPD is wrapped in two plastic bags. For example, the attachment may be attached in a state in which the FPD is wrapped in the first plastic bag, and then the FPD may be wrapped in the second plastic bag. That is, in this case, the attachment is attached from above the plastic bag into which the FPD is wrapped. Thus, the cutter does not come into contact with the first (inner) plastic bag and only the second (outer) plastic bag is incised with the cutter. This enables an old plastic bag to be replaced with a new plastic bag without exposing a detection surface of the FPD.

The first to fourth embodiments described the case in which the pair of rollers 3 is used as the conveyer; however, this case is not a limitation. For example, instead of the pair of rollers 3, the inner wall of the housing 2 may be provided with a rail extending in the vertical direction and a holding member capable of vertically moving on the rail while sandwiching the FPD 100 inserted into the insertion port. In this case, the rail and the holding member function as the conveyer. The conveyer may be implemented with a configuration other than the configurations described in the above as long as such a configuration is capable of sandwiching and vertically conveying a portable medical device such as the FPD 100, the ultrasound probe 400, etc.

According to at least one of the embodiments described in the above, the infection prevention bag that wraps the medical device can be replaced easily.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:
1. A wrap replacing apparatus comprising:
   an insertion port into which a medical device wrapped in a first bag is inserted, the medical device having been used in a state of being wrapped by the first bag;
   a peeler configured to peel off the first bag from the medical device inserted into the insertion port;
   a wrapper configured to wrap in a new second bag, the medical device after the first bag is peeled off; and a take-out port from which the medical device wrapped in the second bag is taken out, wherein the peeler includes a conveyer configured to convey the medical device wrapped in the first bag, the wrap replacing apparatus further includes an inciser configured to incise the first bag wrapping the medical device conveyed by the conveyer, the peeler peels off the first bag incised with the inciser from the medical device, and the conveyer and the peeler correspond to a pair of rollers that sandwiches and conveys the medical device wrapped in the first bag and winds up the first bag peeled off from the medical device.

2. The wrap replacing apparatus according to claim 1, wherein the take-out port is provided at a position different from the insertion port.

3. The wrap replacing apparatus according to claim 1, wherein the inciser is provided at a position facing a side surface of the medical device conveyed by the conveyer.

4. The wrap replacing apparatus according to claim 1, wherein the inciser incises the first bag wrapping the medical device, along a groove provided in the medical device.

5. The wrap replacing apparatus according to claim 4, wherein the inciser includes a side surface inciser that is fixed to an upper side of a central axis of each of the rollers and incises, by the medical device being conveyed by the rollers in a state in which the inciser is disposed inside the groove provided in a side surface of the medical device, a portion that is included in the first bag and is attached to a side surface of the medical device.

6. The wrap replacing apparatus according to claim 4, wherein the inciser includes a bottom surface inciser configured to incise a portion that is included in the first bag and is attached to a bottom surface of the medical device, by moving in a width direction of the medical device, inside a groove provided in the bottom surface of the medical device.

7. The wrap replacing apparatus according to claim 4, wherein the inciser includes an upper surface inciser configured to incise a portion that is included in the first bag and is attached to an upper surface of the medical device, by moving in a width direction of the medical device.

8. The wrap replacing apparatus according to claim 1, wherein an outer peripheral surface of each of the rollers has adhesiveness, and the rollers peel off the first bag from the medical device and wind up the peeled off first bag.

9. The wrap replacing apparatus according to claim 1, wherein each of the rollers includes a protrusion, the first bag includes an engager configured to engage with the protrusion, and by the rollers rotating in a state in which the engager is engaged with the protrusion, the medical device is conveyed while the first bag peeled off from the medical device is wound around each of the rollers.

10. The wrap replacing apparatus according to claim 1, wherein the peeler further includes:

a rotation pin that is provided below each of the rollers and is configured to hook to peel off, by rotating, the first bag attached to the medical device; and a collector configured to collect the first bag hooked on the rotation pin.

11. The wrap replacing apparatus according to claim 1, wherein the first bag includes a fragile portion smaller in strength than a remaining portion, and the fragile portion is provided to a portion attached to a side surface of the medical device and a portion attached to a bottom surface of the medical device.

12. The wrap replacing apparatus according to claim 1, wherein the wrapper is configured to:

fix the second bag to a lower side of the peeler; and seal an opening of the second bag into which the medical device is inserted.

13. The wrap replacing apparatus according to claim 1, wherein the second bag is produced using a sheet that shrinks from heat applied thereto, and the wrapper produces the second bag by shrinking the sheet by applying heat to the sheet in a state in which the medical device is wrapped in the sheet.

14. The wrap replacing apparatus according to claim 1, wherein the medical device is an X-ray detector or an ultrasound probe.

* * * * *